US007803598B2

(12) United States Patent
Kragh et al.

(10) Patent No.: US 7,803,598 B2
(45) Date of Patent: Sep. 28, 2010

(54) CYCLODEXTRIN GLYCOSYLTRANSFERASE (CGTASE) POLYPEPTIDES WITH MODIFIED HYDROLYSIS ACTIVITY

(75) Inventors: Karsten M. Kragh, Viby J (DK); Hans Leemhuis, Cambridge (GB); Lubbert Dijkhuizen, Zuidlaren (NL); Bauke W. Dijkstra, Groningen (NL)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 11/224,218

(22) Filed: Sep. 12, 2005

(65) Prior Publication Data

US 2006/0134266 A1 Jun. 22, 2006

Related U.S. Application Data

(63) Continuation-in-part of application No. PCT/IB2004/001136, filed on Mar. 8, 2004.

(30) Foreign Application Priority Data

Mar. 12, 2003 (GB) ................................ 0305685.0

(51) Int. Cl.
*C12N 9/26* (2006.01)
*C12P 21/06* (2006.01)
*C07H 21/04* (2006.01)
*A23K 97/04* (2006.01)
*A21D 2/00* (2006.01)

(52) U.S. Cl. ............... 435/202; 435/69.1; 536/23.2; 536/23.7; 426/2; 426/20

(58) Field of Classification Search .............. 426/2; 435/204, 252.21, 69.1, 471; 536/23.2
See application file for complete search history.

(56) References Cited

U.S. PATENT DOCUMENTS

| 5,538,882 | A |   | 7/1996  | Ishikawa et al. |         |
|-----------|---|---|---------|-----------------|---------|
| 6,004,790 | A | * | 12/1999 | Dijkhuizen et al. | 435/193 |
| 6,162,628 | A | * | 12/2000 | Cherry et al.   | 435/202 |
| 6,482,622 | B1|   | 11/2002 | Frandsen et al. |         |

OTHER PUBLICATIONS

Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence and structure. Q. Rev. Biophys., 2003, vol. 36(3): 307-340.* van der Veen et al., Rational design of cyclodextrin glycosyltransferase from *Bacillus circulans* 251 to increase alpha-cyclodextrin production. J. Mol. Biol., 2000, vol. 296: 1027-1038.*
van der Veen et al., The transglycosylation reactions catalyzed by cyclodextrin glycosyltransferase from *Bacillus circulans* (starin 251) proceed via different kinetic mechanisms. Eur. J. Biochem., 2000,vol. 267: 658-665.*
van der Veen et al., Hydrophobic amino acid residues in the acceptor binding site are main determinants for reaction mechanism and specificity of cyclodextrin-glycosyltransferase. JBC., 2001, vol. 276 (48): 44557-44562.*
Uitdehaag et al., Catalytic mechanism and product specificty of cyclodextrin glycosyltransferase, a prtotypical transglycosylase from alpha-amylase family. Enzyme Microbiol. Technol., 2002, vol. 30: 295-304.*
Klein et al., Structure of cyclodextrin glycosyltransferase refined at 2.0 A resolution. J. Mol. Biol., 1991, vol. 217: 737-750.*
Diderichsen et al., Cloning of a malotogenic alpha-amyalse from *Bacillus stearothermophilus*. FEMS Microbiol., 1988, vol. 56: 53-60.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Leemhuis Hans, et al.; "Conversion of cyclodextrin glycosyltransferase into a starch hydrolase by directed evolution: The role of alanine 230 in acceptor subsite +1"; Biochemistry (2003); vol. 42(24); pp. 7518-7526.
Veen, et al.; "Hydrophobic amino acid residues in the acceptor binding site are main determinants for reaction mechanism and specificity of cyclodextrin-glycosyltransferase"; Journal of biological Chemistry(2001); vol. 276(48); pp. 44557-44562.
Henrissat, B. and Davies, G. (1997) *Curr. Opin. Struct. Biol.* 7: 637-644.
McCarter, J. D. and Withers, S. G. (1994) *Curr. Opin. Struct. Biol.* 4: 885-892.
Uitdehaag, J. C. M., et al. (1999) *Nature Struct. Biol.* 6: 432-436.
Kuriki, T. and Imanaka, T. (1999) *J. Biosci. Bioeng.* 87: 557-565.
Penninga, D., et al. (1996) *J Biol. Chem.* 271: 32777-32784.
Ohdan, K., et al. (2000) *Appl. Environ. Microbiol.* 66: 3058-3064.
Wind, et al. (1995) *Appl. Environm. Microbiol.* 61: 1257-1265.
Van Der Veen, B. A., et al. (2000) *Eur. J. Biochem.* 267: 658-665.
Nakamura, et al., 1994, *Biochemistry*, 33: 9926-9936.
Leemhius, et al. (2002) *FEBS letters* 514: 189-192.

* cited by examiner

*Primary Examiner*—Ganapathirama Raghu
(74) *Attorney, Agent, or Firm*—Frommer Lawrence & Haug LLP; Thomas J. Kowalski; Heather J. DiPietrantonio

(57) ABSTRACT

An enzyme is described which enzyme is derived from family 13 of α-amylases. The enzyme variant is obtainable by modifying a CGTase or a maltogenic α-amylase. The enzyme is useful in preparing a food or a food product such as bakery products.

5 Claims, 5 Drawing Sheets

Figure 1:
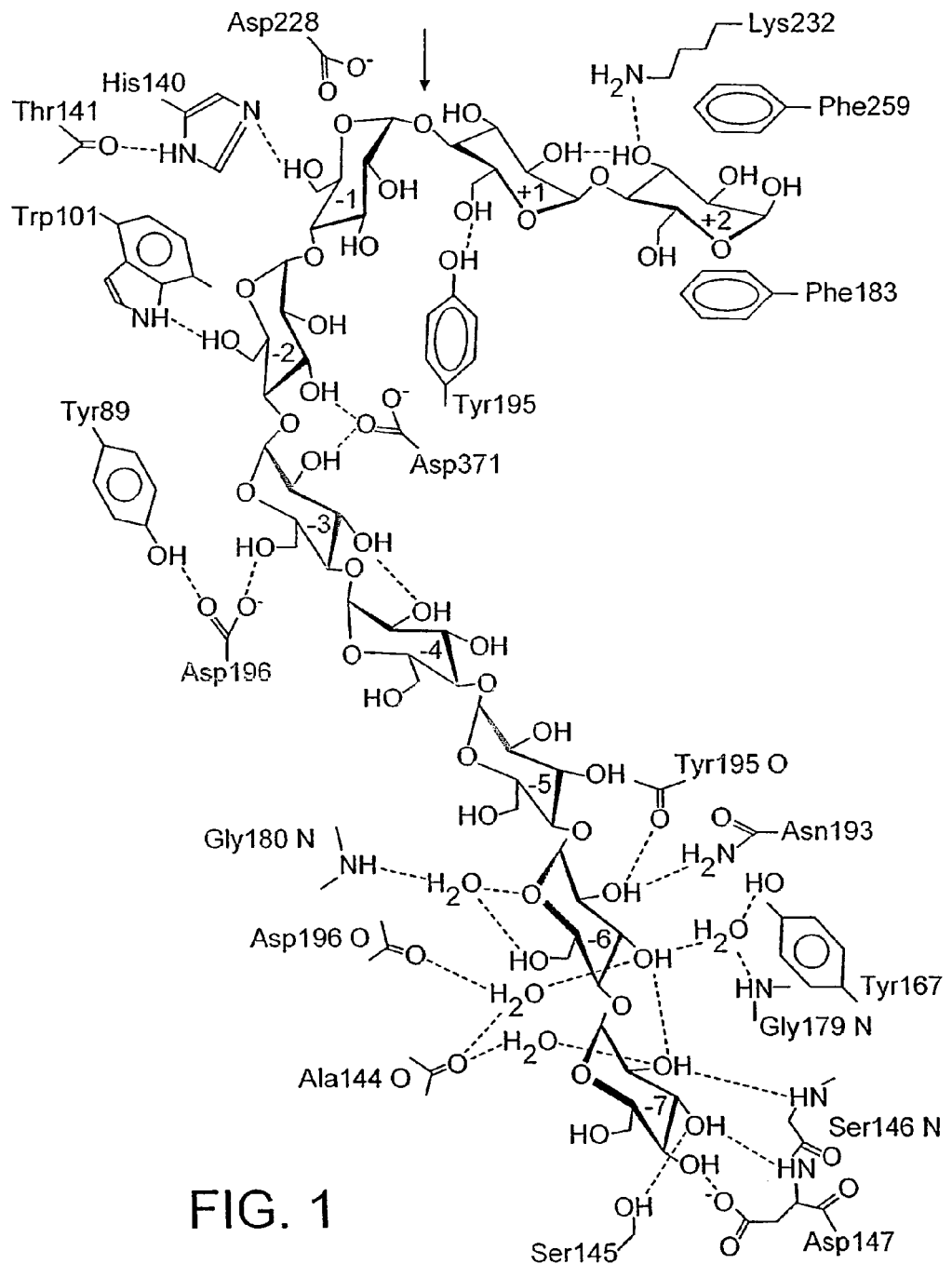

```
         10        20        30        40        50        60        70        80
-----SSSASVKGDVIYQIIIDRFYDGDTTNNNPAKSYGLYDPTKSKWKMYWGGDIEGVRQKL---PYLKQLGVTTIWLS  72
ASDTAVSNVVNYSTDVIYQIVTDRFVDGNTSNNPT---GDLYDPTHTSLKKYFGGDWQGIINKINDGYLTGMVTAIWIS  77
APDTSVSNVVNYSTDVIYQIVTDRFLDGNPSNNPT---GDLYDPTHTSLKKIFGGDWQGIINKINDGYLTGMGITAIWIS  77
APDTSVSNKQNFSTDVIYQIFTDRFSDGNPANNPT---GAAAFDGTCTNLRLYCGGDWQGIINKINDGYLTGMGVTAIWIS  77
                                    GAAAFDGTCTNLRLYCGGDWQGIINKINDGYLTGMGVTAIWIS

PVLDNLDTLAGT-----DNTGYHGYWTRDFKQIEEHFGNWTTFDTLVNDAHQNGIKVIVDFVPNHSTPFKANDSTFAEGGA  148
QPVENIYAVLPDSTFGGSTSYHGYWARDFKKRTNPYFGSETDFQNLINTAHAHNIKVIIDFAPNHTSPASETDPTYAENGR  157
QPVENIYAVLPDSTFGGSTSYHGYWARDFKKTNPFFGSFTDFQNLIATAHAHNIKVIIDFAPNHTSPASETDPTYGENGR  157
QPVENIYSIINYSG-VNNTAYHGYWARDFKKTNPAYGTIADFQNLIAAAHAKNIKVIIDFAPNHTSPASSDQPSFAENGR  156

LYNNGTYMGNYFDDATKGYFHHNGDISNWDDRYEAQWKNFTDPAGFSLADLSQENGTIAQYLTDAAVQLVAHGADGLRID  228
LYDNGTLLGGYTNDT-NGYFHHYGGTD-FSSYEDGIYRNLF-----DLADLNQQNSTIDSYLKSAIKVWLDMGIDGIRLD  230
LYDNGTLLGGYTNDT-NGYFHHYGGTN-FSSYEDGIYRNLF-----DLADLDQQNSTIDSYLKAAIKLWLDMGIDGIRMD  230
LYDNGTLLGGYTNDT-QNLFHHNGGTD-FSTTENGIYKNLY-----DLADLNHNNSTVDVYLKDAIKMWLDLGIDGIRMD  229

AVKHFNSGFSKSLADKLYQKKDIFLVGEWYGDD-PGTANHLEKVRYANNSGVNVLDFDLNTVIRNVFGTFTQTMYDLNNM  307
AVKHMPFGWQKNFMDSILSYRPVFTFGEWFLG-TNEI--DVNNTYFANESGMSLLDERFSQKVRQVFRDNTDTMYGLDSM  307
AVKHMAFGWQKNFMDSILSYRPVFTFGEWYLG-TNEV--DPNNTYFANESGMSLLDFRFAQKVRQVFRDNTDTMYGLDSM  307
AVKHMPFGWQKSFMAAVNNYKPVFTFGEWFLG-VNEV--SPENHKFANESGMSLLDFRFAQKVRQVFRDNTDNMYGLKAM  306

VNQTGNEYKYKENLITFIDNHDMSRFLSVNSNKANLHQALAFILTSRGTPSIYYGTEQYMAGGNDPYNRGMMPAFDTTTT  387
IQSTASDYNFINDMVTFIDNHDMDRFYN-GGSTRPVEQLAFTLTSRGVPAIYYGTEQYMTGNGDPYNRAMMTSENTSTT  386
IQSTAADYNFINDMVTFIDNHDMDRFYT-GGSTRPVEQALAFTLTSRGVPAIYYGTEQYMTGNGDPYNRAMMTSFDTTTT  386
LEGSAADYAQVDDQVTFIDNHDMERFHASANANRRKLEQALAFTLTSRGVPAIYYGTEQYMSGGTDPDNRARIPSFSTST  386
```

FIG. 5

```
AFKEVSTLAGLRRNNAAIQYGTTTQRWINNDVYIYEPKFFNDVVLVAINRNTQSSYSISGLQTALPNGSYADYLSGLLGG    467
AYNVIKKLAPLRKSNPAIAYGTTQQRWINNDVYIYEPKFGNNVALVAINRNLSTSYNITGLYTALPAGTYTDVLGGLLNG    466
AYNVIKKLAPLRKSNPAIAYGTQKQRWINNDVYIYERQFGNNVALVAINRNLSTSYIITGLYTALPAGTYSDMLGGLLNG    466
AYQVIQKLAPLRKCNPAIAYGSTQERWINNDVLITERKFGSNVAVAVAVNRNLNAPASISGLVTSLPQGSYNDVLGGLLNG    466
NGISVS-NGSVASFTLAPGAVSWQYST-SASAPQIGSVAPNMGIPGNVVTIDGKFGFGTTQGTVTFGGVTAT---VKSWT   543
NSISVASDGSVTPFTLSAGEVAVWQYVSSSN-SPLIGHVGPTMTKAGQTITIDGRGFGTTSGQVLFGSTAGT---IVSWD   542
SSITVSSNGSVTPFTLAPGEVAVWQYVSTTN-PPLIGHVGPTMTKAGQTITIDGRGFGTTAGQVLFGTTPAT---IVSWE   542
NTLSVGSGGAASNFTLAAGGTAVWQYTAATA-TPTIGHVGPMMAKPGVTITIDGRGFGSSKGTVYFGTTAVSGADITSWE   545

SNRIEVYVPNMAAGLTDVKVTA-GGVSSNLYS-INILSGTQTSVVFTVKSAPPTNLGDKIYLTGNIPELGNWSTDTSGAV   620
DTEVKVKVPSVTPGKYNISLKTSSGATSNTYNNINILTGNQICVRFVVNNASTVY-GENVYLTGNVAELGNWDTS----   616
DTEVKVKVPALTPGKYNITLKTASGVTSNSYNNINVLTGNQVCVRFVVNNATTVW-GENVYLTGNVAELGNWDTS----   616
DTQIKVKIPAVAGGNYNIKVANAAGTASNVIDNFEVLSGDQVSVRFVVNNATTAL-GQNVYLTGSVSELGNWDPA----   619

NNAQGPLLAP---NYPDWFYVESVPAGTTIQFKFFIKPADGT-IQWENGSNHVATTPTGATGNITVTWQN   686
-KAIGPMFNQVVYQYPTWYYDVSVPAGTTIQFKFFIKKN--GNTITWEGGSNHTITTVPSSSTGTVIVNWQQ   683
-KAIGPMFNQVVYQYPTWYYDVSVPAGTTIEFKFIKKN---GSTVTWEGGYNHVYTTPTSGTATVIVDWQP   683
-KAIGPMYNQVVYQYPTWYYDVSVPAGTTIEFKFLKKQ---GSTVTWEGGSNHTFTAPSSGTATINVWQP   686
```

FIG. 6

SEQUENCE LISTING

<160> NUMBER OF SEQ ID NOS: 17

<210> SEQ ID NO 1
<211> LENGTH: 686
<212> TYPE: PRT
<213> ORGANISM: Bacillus circulans

```
<400> SEQUENCE: 1

Ala Pro Asp Thr Ser Val Ser Asn Lys Gln Asn Phe Ser Thr Asp Val
 1               5                  10                  15

Ile Tyr Gln Ile Phe Thr Asp Arg Phe Ser Asp Gly Asn Pro Ala Asn
             20                  25                  30

Asn Pro Thr Gly Ala Ala Phe Asp Gly Thr Cys Thr Asn Leu Arg Leu
         35                  40                  45

Tyr Cys Gly Gly Asp Trp Gln Gly Ile Ile Asn Lys Ile Asn Asp Gly
 50                  55                  60

Tyr Leu Thr Gly Met Gly Val Thr Ala Ile Trp Ile Ser Gln Pro Val
 65                  70                  75                  80

Glu Asn Ile Tyr Ser Ile Ile Asn Tyr Ser Gly Val Asn Asn Thr Ala
                 85                  90                  95

Tyr His Gly Tyr Trp Ala Arg Asp Phe Lys Lys Thr Asn Pro Ala Tyr
             100                 105                 110

Gly Thr Ile Ala Asp Phe Gln Asn Leu Ile Ala Ala His Ala Lys
             115                 120                 125

Asn Ile Lys Val Ile Ile Asp Phe Ala Pro Asn His Thr Ser Pro Ala
130                 135                 140

Ser Ser Asp Gln Pro Ser Phe Ala Glu Asn Gly Arg Leu Tyr Asp Asn
145                 150                 155                 160

Gly Thr Leu Leu Gly Gly Tyr Thr Asn Asp Thr Gln Asn Leu Phe His
                 165                 170                 175

His Asn Gly Gly Thr Asp Phe Ser Thr Thr Glu Asn Gly Ile Tyr Lys
             180                 185                 190

Asn Leu Tyr Asp Leu Ala Asp Leu Asn His Asn Asn Ser Thr Val Asp
             195                 200                 205

Val Tyr Leu Lys Asp Ala Ile Lys Met Trp Leu Asp Leu Gly Ile Asp
210                 215                 220

Gly Ile Arg Met Asp Val Val Lys His Met Pro Phe Gly Trp Gln Lys
225                 230                 235                 240

Ser Phe Met Ala Ala Val Asn Asn Tyr Lys Pro Val Phe Thr Phe Gly
                 245                 250                 255

Glu Trp Phe Leu Gly Val Asn Glu Val Ser Pro Glu Asn His Lys Phe
             260                 265                 270

Ala Asn Glu Ser Gly Met Ser Leu Leu Asp Phe Arg Phe Ala Gln Lys
             275                 280                 285

Val Arg Gln Val Phe Arg Asp Asn Thr Asp Asn Met Tyr Gly Leu Lys
             290                 295                 300

Ala Met Leu Glu Gly Ser Ala Ala Asp Tyr Ala Gln Val Asp Asp Gln
305                 310                 315                 320

Val Thr Phe Ile Asp Asn His Asp Met Glu Arg Phe His Ala Ser Asn
                 325                 330                 335

Ala Asn Arg Arg Lys Leu Glu Gln Ala Leu Ala Phe Thr Leu Thr Ser
             340                 345                 350

Arg Gly Val Pro Ala Ile Tyr Tyr Gly Thr Glu Gln Tyr Met Ser Gly
             355                 360                 365

Gly Thr Asp Pro Asp Asn Arg Ala Arg Ile Pro Ser Phe Ser Thr Ser
         370                 375                 380

Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
```

-continued

```
                405                 410                 415
Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
            435                 440                 445

Thr Ser Leu Pro Gln Gly Ser Tyr Asn Asp Val Leu Gly Gly Leu Leu
            450                 455                 460

Asn Gly Asn Thr Leu Ser Val Gly Ser Gly Ala Ala Ser Asn Phe
465                 470                 475                 480

Thr Leu Ala Ala Gly Gly Thr Ala Val Trp Gln Tyr Thr Ala Ala Thr
                485                 490                 495

Ala Thr Pro Thr Ile Gly His Val Gly Pro Met Met Ala Lys Pro Gly
            500                 505                 510

Val Thr Ile Thr Ile Asp Gly Arg Gly Phe Gly Ser Ser Lys Gly Thr
            515                 520                 525

Val Tyr Phe Gly Thr Thr Ala Val Ser Gly Ala Asp Ile Thr Ser Trp
            530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
                565                 570                 575

Asp Asn Phe Glu Val Leu Ser Gly Asp Gln Val Ser Val Arg Phe Val
            580                 585                 590

Val Asn Asn Ala Thr Thr Ala Leu Gly Gln Asn Val Tyr Leu Thr Gly
            595                 600                 605

Ser Val Ser Glu Leu Gly Asn Trp Asp Pro Ala Lys Ala Ile Gly Pro
            610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln
                645                 650                 655

Gly Ser Thr Val Thr Trp Glu Gly Gly Ser Asn His Thr Phe Thr Ala
            660                 665                 670

Pro Ser Ser Gly Thr Ala Thr Ile Asn Val Asn Trp Gln Pro
            675                 680                 685

<210> SEQ ID NO 2
<211> LENGTH: 683
<212> TYPE: PRT
<213> ORGANISM: Thermoanaerobacterium thermosulfurigenes

<400> SEQUENCE: 2

Ala Ser Asp Thr Ala Val Ser Asn Val Val Asn Tyr Ser Thr Asp Val
1               5                   10                  15

Ile Tyr Gln Ile Val Thr Asp Arg Phe Val Asp Gly Asn Thr Ser Asn
                20                  25                  30

Asn Pro Thr Gly Asp Leu Tyr Asp Pro Thr His Thr Ser Leu Lys Lys
            35                  40                  45

Tyr Phe Gly Gly Asp Trp Gln Gly Ile Ile Asn Lys Ile Asn Asp Gly
        50                  55                  60

Tyr Leu Thr Gly Met Gly Val Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95
```

-continued

```
Ser Tyr His Gly Tyr Trp Ala Arg Asp Phe Lys Arg Thr Asn Pro Tyr
            100                 105                 110

Phe Gly Ser Phe Thr Asp Phe Gln Asn Leu Ile Asn Thr Ala His Ala
        115                 120                 125

His Asn Ile Lys Val Ile Asp Phe Ala Pro Asn His Thr Ser Pro
130                 135                 140

Ala Ser Glu Thr Asp Pro Thr Tyr Ala Glu Asn Gly Arg Leu Tyr Asp
145                 150                 155                 160

Asn Gly Thr Leu Leu Gly Gly Tyr Thr Asn Asp Thr Asn Gly Tyr Phe
                165                 170                 175

His His Tyr Gly Gly Thr Asp Phe Ser Ser Tyr Glu Asp Gly Ile Tyr
            180                 185                 190

Arg Asn Leu Phe Asp Leu Ala Asp Leu Asn Gln Gln Asn Ser Thr Ile
        195                 200                 205

Asp Ser Tyr Leu Lys Ser Ala Ile Lys Val Trp Leu Asp Met Gly Ile
    210                 215                 220

Asp Gly Ile Arg Leu Asp Val Val Lys His Met Pro Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Phe Leu Gly Thr Asn Glu Ile Asp Val Asn Asn Thr Tyr
            260                 265                 270

Phe Ala Asn Glu Ser Gly Met Ser Leu Leu Asp Phe Arg Phe Ser Gln
        275                 280                 285

Lys Val Arg Gln Val Phe Arg Asp Asn Thr Asp Thr Met Tyr Gly Leu
    290                 295                 300

Asp Ser Met Ile Gln Ser Thr Ala Ser Asp Tyr Asn Phe Ile Asn Asp
305                 310                 315                 320

Met Val Thr Phe Ile Asp Asn His Asp Met Asp Arg Phe Tyr Asn Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
        355                 360                 365

Asn Gly Asp Pro Tyr Asn Arg Ala Met Met Thr Ser Phe Asn Thr Ser
    370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Thr Gln Gln Arg Trp Ile Asn Asn
                405                 410                 415

Asp Val Tyr Ile Tyr Glu Arg Lys Phe Gly Asn Asn Val Ala Leu Val
            420                 425                 430

Ala Ile Asn Arg Asn Leu Ser Thr Ser Tyr Asn Ile Thr Gly Leu Tyr
        435                 440                 445

Thr Ala Leu Pro Ala Gly Thr Tyr Thr Asp Val Leu Gly Gly Leu Leu
    450                 455                 460

Asn Gly Asn Ser Ile Ser Val Ala Ser Asp Gly Ser Val Thr Pro Phe
465                 470                 475                 480

Thr Leu Ser Ala Gly Glu Val Ala Val Trp Gln Tyr Val Ser Ser Ser
                485                 490                 495

Asn Ser Pro Leu Ile Gly His Val Gly Pro Thr Met Thr Lys Ala Gly
            500                 505                 510

Gln Thr Ile Thr Ile Asp Gly Arg Gly Phe Gly Thr Thr Ser Gly Gln
```

```
                515                 520                 525
Val Leu Phe Gly Ser Thr Ala Gly Thr Ile Val Ser Trp Asp Asp Thr
    530                 535                 540

Glu Val Lys Val Lys Val Pro Ser Val Thr Pro Gly Lys Tyr Asn Ile
545                 550                 555                 560

Ser Leu Lys Thr Ser Ser Gly Ala Thr Ser Asn Thr Tyr Asn Asn Ile
                565                 570                 575

Asn Ile Leu Thr Gly Asn Gln Ile Cys Val Arg Phe Val Val Asn Asn
                580                 585                 590

Ala Ser Thr Val Tyr Gly Glu Asn Val Tyr Leu Thr Gly Asn Val Ala
                595                 600                 605

Glu Leu Gly Asn Trp Asp Thr Ser Lys Ala Ile Gly Pro Met Phe Asn
        610                 615                 620

Gln Val Val Tyr Gln Tyr Pro Thr Trp Tyr Tyr Asp Val Ser Val Pro
625                 630                 635                 640

Ala Gly Thr Thr Ile Gln Phe Lys Phe Ile Lys Lys Asn Gly Asn Thr
                645                 650                 655

Ile Thr Trp Glu Gly Gly Ser Asn His Thr Tyr Thr Val Pro Ser Ser
            660                 665                 670

Ser Thr Gly Thr Val Ile Val Asn Trp Gln Gln
            675                 680

<210> SEQ ID NO 3
<211> LENGTH: 686
<212> TYPE: PRT
<213> ORGANISM: Artificial Sequence
<220> FEATURE:
<223> OTHER INFORMATION: Variant maltogenic alpha maylase

<400> SEQUENCE: 3

Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
                20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
        50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
                100                 105                 110

Leu Val Asn Asp Ala His Gln Asn Gly Ile Lys Val Ile Val Asp Phe
            115                 120                 125

Val Pro Asn His Ser Thr Pro Phe Lys Ala Asn Asp Ser Thr Phe Ala
130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
```

-continued

```
                195                 200                 205
Tyr Leu Thr Asp Ala Ala Val Gln Leu Val Ala His Gly Ala Asp Gly
    210                 215                 220

Leu Arg Ile Asp Val Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
                290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Pro Ala Phe Asp Thr
                370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
                435                 440                 445

Gln Thr Ala Leu Pro Asn Gly Ser Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
                500                 505                 510

Asn Val Val Thr Ile Asp Gly Lys Gly Phe Gly Thr Thr Gln Gly Thr
                515                 520                 525

Val Thr Phe Gly Gly Val Thr Ala Thr Val Lys Ser Trp Thr Ser Asn
    530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
                595                 600                 605

Leu Gly Asn Trp Ser Thr Asp Ser Gly Ala Val Asn Asn Ala Gln
    610                 615                 620
```

```
Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
            645                 650                 655

Asp Gly Thr Ile Gln Trp Glu Asn Gly Ser Asn His Val Ala Thr Thr
        660                 665                 670

Pro Thr Gly Ala Thr Gly Asn Ile Thr Val Thr Trp Gln Asn
            675                 680                 685

<210> SEQ ID NO 4
<211> LENGTH: 686
<212> TYPE: PRT
<213> ORGANISM: Bacillus circulans

<400> SEQUENCE: 4

Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
            20                  25                  30

Asn Pro Thr Gly Ala Ala Phe Asp Gly Thr Cys Thr Asn Leu Arg Leu
        35                  40                  45

Tyr Cys Gly Gly Asp Trp Gln Gly Ile Ile Asn Lys Ile Asn Asp Gly
    50                  55                  60

Tyr Leu Thr Gly Met Gly Val Thr Ala Ile Trp Ile Ser Gln Pro Val
65                  70                  75                  80

Glu Asn Ile Tyr Ser Ile Ile Asn Tyr Ser Gly Val Asn Asn Thr Ala
                85                  90                  95

Tyr His Gly Tyr Trp Ala Arg Asp Phe Lys Lys Thr Asn Pro Ala Tyr
            100                 105                 110

Gly Thr Ile Ala Asp Phe Gln Asn Leu Ile Ala Ala Ala His Ala Lys
        115                 120                 125

Asn Ile Lys Val Ile Ile Asp Phe Ala Pro Asn His Thr Ser Pro Ala
130                 135                 140

Ser Ser Asp Gln Pro Ser Phe Ala Glu Asn Gly Arg Leu Tyr Asp Asn
145                 150                 155                 160

Gly Thr Leu Leu Gly Gly Tyr Thr Asn Asp Thr Gln Asn Leu Phe His
                165                 170                 175

His Asn Gly Gly Thr Asp Phe Ser Thr Thr Glu Asn Gly Ile Tyr Lys
            180                 185                 190

Asn Leu Tyr Asp Leu Ala Asp Leu Asn His Asn Asn Ser Thr Val Asp
        195                 200                 205

Val Tyr Leu Lys Asp Ala Ile Lys Met Trp Leu Asp Leu Gly Ile Asp
    210                 215                 220

Gly Ile Arg Met Asp Ala Val Lys His Met Pro Phe Gly Trp Gln Lys
225                 230                 235                 240

Ser Phe Met Ala Ala Val Asn Asn Tyr Lys Pro Val Phe Thr Phe Gly
                245                 250                 255

Glu Trp Phe Leu Gly Val Asn Glu Val Ser Pro Glu Asn His Lys Phe
            260                 265                 270

Ala Asn Glu Ser Gly Met Ser Leu Leu Asp Phe Arg Phe Ala Gln Lys
        275                 280                 285

Val Arg Gln Val Phe Arg Asp Asn Thr Asp Asn Met Tyr Gly Leu Lys
    290                 295                 300

Ala Met Leu Glu Gly Ser Ala Ala Asp Tyr Ala Gln Val Asp Asp Gln
```

```
              305                 310                 315                 320
Val Thr Phe Ile Asp Asn His Asp Met Glu Arg Phe His Ala Ser Asn
                325                 330                 335

Ala Asn Arg Arg Lys Leu Glu Gln Ala Leu Ala Phe Thr Leu Thr Ser
            340                 345                 350

Arg Gly Val Pro Ala Ile Tyr Tyr Gly Thr Glu Gln Tyr Met Ser Gly
        355                 360                 365

Gly Thr Asp Pro Asp Asn Arg Ala Arg Ile Pro Ser Phe Ser Thr Ser
    370                 375                 380

Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
                405                 410                 415

Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
        435                 440                 445

Thr Ser Leu Pro Gln Gly Ser Tyr Asn Asp Val Leu Gly Gly Leu Leu
    450                 455                 460

Asn Gly Asn Thr Leu Ser Val Gly Ser Gly Ala Ala Ser Asn Phe
465                 470                 475                 480

Thr Leu Ala Ala Gly Gly Thr Ala Val Trp Gln Tyr Thr Ala Ala Thr
                485                 490                 495

Ala Thr Pro Thr Ile Gly His Val Gly Pro Met Met Ala Lys Pro Gly
            500                 505                 510

Val Thr Ile Thr Ile Asp Gly Arg Gly Phe Gly Ser Ser Lys Gly Thr
        515                 520                 525

Val Tyr Phe Gly Thr Thr Ala Val Ser Gly Ala Asp Ile Thr Ser Trp
    530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
                565                 570                 575

Asp Asn Phe Glu Val Leu Ser Gly Asp Gln Val Ser Val Arg Phe Val
            580                 585                 590

Val Asn Asn Ala Thr Thr Ala Leu Gly Gln Asn Val Tyr Leu Thr Gly
        595                 600                 605

Ser Val Ser Glu Leu Gly Asn Trp Asp Pro Ala Lys Ala Ile Gly Pro
    610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln
                645                 650                 655

Gly Ser Thr Val Thr Trp Glu Gly Gly Ser Asn His Thr Phe Thr Ala
            660                 665                 670

Pro Ser Ser Gly Thr Ala Thr Ile Asn Val Asn Trp Gln Pro
        675                 680                 685

<210> SEQ ID NO 5
<211> LENGTH: 683
<212> TYPE: PRT
<213> ORGANISM: Thermoanaerobacterium thermosulfurigenes

<400> SEQUENCE: 5
```

-continued

```
Ala Ser Asp Thr Ala Val Ser Asn Val Val Asn Tyr Ser Thr Asp Val
1               5                   10                  15

Ile Tyr Gln Ile Val Thr Asp Arg Phe Val Asp Gly Asn Thr Ser Asn
            20                  25                  30

Asn Pro Thr Gly Asp Leu Tyr Asp Pro Thr His Thr Ser Leu Lys Lys
        35                  40                  45

Tyr Phe Gly Gly Asp Trp Gln Gly Ile Ile Asn Lys Ile Asn Asp Gly
    50                  55                  60

Tyr Leu Thr Gly Met Gly Val Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Arg Thr Asn Pro Tyr
            100                 105                 110

Phe Gly Ser Phe Thr Asp Phe Gln Asn Leu Ile Asn Thr Ala His Ala
        115                 120                 125

His Asn Ile Lys Val Ile Ile Asp Phe Ala Pro Asn His Thr Ser Pro
    130                 135                 140

Ala Ser Glu Thr Asp Pro Thr Tyr Ala Glu Asn Gly Arg Leu Tyr Asp
145                 150                 155                 160

Asn Gly Thr Leu Leu Gly Gly Tyr Thr Asn Asp Thr Asn Gly Tyr Phe
                165                 170                 175

His His Tyr Gly Gly Thr Asp Phe Ser Ser Tyr Glu Asp Gly Ile Tyr
            180                 185                 190

Arg Asn Leu Phe Asp Leu Ala Asp Leu Asn Gln Gln Asn Ser Thr Ile
        195                 200                 205

Asp Ser Tyr Leu Lys Ser Ala Ile Lys Val Trp Leu Asp Met Gly Ile
    210                 215                 220

Asp Gly Ile Arg Leu Asp Ala Val Lys His Met Pro Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Phe Leu Gly Thr Asn Glu Ile Asp Val Asn Asn Thr Tyr
            260                 265                 270

Phe Ala Asn Glu Ser Gly Met Ser Leu Leu Asp Phe Arg Phe Ser Gln
        275                 280                 285

Lys Val Arg Gln Val Phe Arg Asp Asn Thr Asp Thr Met Tyr Gly Leu
    290                 295                 300

Asp Ser Met Ile Gln Ser Thr Ala Ser Asp Tyr Asn Phe Ile Asn Asp
305                 310                 315                 320

Met Val Thr Phe Ile Asp Asn His Asp Met Asp Arg Phe Tyr Asn Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
        355                 360                 365

Asn Gly Asp Pro Tyr Asn Arg Ala Met Met Thr Ser Phe Asn Thr Ser
    370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Thr Gln Gln Arg Trp Ile Asn Asn
                405                 410                 415

Asp Val Tyr Ile Tyr Glu Arg Lys Phe Gly Asn Asn Val Ala Leu Val
```

```
                    420             425             430
Ala Ile Asn Arg Asn Leu Ser Thr Ser Tyr Asn Ile Thr Gly Leu Tyr
            435             440             445

Thr Ala Leu Pro Ala Gly Thr Tyr Thr Asp Val Leu Gly Gly Leu Leu
        450             455             460

Asn Gly Asn Ser Ile Ser Val Ala Ser Asp Gly Ser Val Thr Pro Phe
465             470             475             480

Thr Leu Ser Ala Gly Glu Val Ala Val Trp Gln Tyr Val Ser Ser Ser
                485             490             495

Asn Ser Pro Leu Ile Gly His Val Gly Pro Thr Met Thr Lys Ala Gly
            500             505             510

Gln Thr Ile Thr Ile Asp Gly Arg Gly Phe Gly Thr Thr Ser Gly Gln
        515             520             525

Val Leu Phe Gly Ser Thr Ala Gly Thr Ile Val Ser Trp Asp Asp Thr
    530             535             540

Glu Val Lys Val Lys Val Pro Ser Val Thr Pro Gly Lys Tyr Asn Ile
545             550             555             560

Ser Leu Lys Thr Ser Ser Gly Ala Thr Ser Asn Thr Tyr Asn Asn Ile
                565             570             575

Asn Ile Leu Thr Gly Asn Gln Ile Cys Val Arg Phe Val Val Asn Asn
            580             585             590

Ala Ser Thr Val Tyr Gly Glu Asn Val Tyr Leu Thr Gly Asn Val Ala
        595             600             605

Glu Leu Gly Asn Trp Asp Thr Ser Lys Ala Ile Gly Pro Met Phe Asn
    610             615             620

Gln Val Val Tyr Gln Tyr Pro Thr Trp Tyr Tyr Asp Val Ser Val Pro
625             630             635             640

Ala Gly Thr Thr Ile Gln Phe Lys Phe Ile Lys Lys Asn Gly Asn Thr
                645             650             655

Ile Thr Trp Glu Gly Gly Ser Asn His Thr Tyr Thr Val Pro Ser Ser
            660             665             670

Ser Thr Gly Thr Val Ile Val Asn Trp Gln Gln
        675             680

<210> SEQ ID NO 6
<211> LENGTH: 686
<212> TYPE: PRT
<213> ORGANISM: Bacillus sp.

<400> SEQUENCE: 6

Ser Ser Ser Ala Ser Val Lys Gly Asp Val Ile Tyr Gln Ile Ile
1               5                   10                  15

Asp Arg Phe Tyr Asp Gly Asp Thr Thr Asn Asn Pro Ala Lys Ser
            20              25              30

Tyr Gly Leu Tyr Asp Pro Thr Lys Ser Lys Trp Lys Met Tyr Trp Gly
        35              40              45

Gly Asp Leu Glu Gly Val Arg Gln Lys Leu Pro Tyr Leu Lys Gln Leu
    50              55              60

Gly Val Thr Thr Ile Trp Leu Ser Pro Val Leu Asp Asn Leu Asp Thr
65              70              75              80

Leu Ala Gly Thr Asp Asn Thr Gly Tyr His Gly Tyr Trp Thr Arg Asp
                85              90              95

Phe Lys Gln Ile Glu Glu His Phe Gly Asn Trp Thr Thr Phe Asp Thr
            100             105             110
```

```
Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
    210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
    370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
            420                 425                 430

Val Ala Ile Asn Arg Asn Thr Gln Ser Ser Tyr Ser Ile Ser Gly Leu
        435                 440                 445

Gln Thr Ala Leu Pro Asn Gly Ser Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
        515                 520                 525

Val Thr Phe Gly Gly Val Thr Ala Thr Val Lys Ser Trp Thr Ser Asn
```

```
              530                 535                 540
Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
                595                 600                 605

Leu Gly Asn Trp Ser Thr Asp Thr Ser Gly Ala Val Asn Asn Ala Gln
                610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
                660                 665                 670

Pro Thr Gly Ala Thr Gly Asn Ile Thr Val Thr Trp Gln Asn
                675                 680                 685

<210> SEQ ID NO 7
<211> LENGTH: 36
<212> TYPE: DNA
<213> ORGANISM: Artificial Sequence
<220> FEATURE:
<223> OTHER INFORMATION: F1 (XhoI) primer

<400> SEQUENCE: 7
gcgccggata cctcgagttc aacaagcaa aatttc                              36

<210> SEQ ID NO 8
<211> LENGTH: 36
<212> TYPE: DNA
<213> ORGANISM: Bacillus sp.

<400> SEQUENCE: 8
ccaattcacg ttaatggtac cggtgccgct ggacgg                             36

<210> SEQ ID NO 9
<211> LENGTH: 27
<212> TYPE: DNA
<213> ORGANISM: Artificial Sequence
<220> FEATURE:
<223> OTHER INFORMATION: F21L primer

<400> SEQUENCE: 9
atctatcaaa ttttgaccga caggttt                                       27

<210> SEQ ID NO 10
<211> LENGTH: 21
<212> TYPE: DNA
<213> ORGANISM: Artificial Sequence
<220> FEATURE:
<223> OTHER INFORMATION: R47W primer

<400> SEQUENCE: 10
acgaacctct ggctgtattg c                                             21

<210> SEQ ID NO 11
<211> LENGTH: 24
<212> TYPE: DNA
```

```
<213> ORGANISM: Artificial Sequence
<220> FEATURE:
<223> OTHER INFORMATION: N94S primer

<400> SEQUENCE: 11
tccggcgtga acagcacggc ctat                                            24

<210> SEQ ID NO 12
<211> LENGTH: 21
<212> TYPE: DNA
<213> ORGANISM: Artificial Sequence
<220> FEATURE:
<223> OTHER INFORMATION: A245T primer

<400> SEQUENCE: 12
tttatggcta ccgtcaacaa c                                               21

<210> SEQ ID NO 13
<211> LENGTH: 21
<212> TYPE: DNA
<213> ORGANISM: Artificial Sequence
<220> FEATURE:
<223> OTHER INFORMATION: Q320L primer

<400> SEQUENCE: 13
gtggatgacc tggtgacgtt c                                               21

<210> SEQ ID NO 14
<211> LENGTH: 21
<212> TYPE: DNA
<213> ORGANISM: Artificial Sequence
<220> FEATURE:
<223> OTHER INFORMATION: A357T primer

<400> SEQUENCE: 14
ggcgtcccca ccatttatta c                                               21

<210> SEQ ID NO 15
<211> LENGTH: 21
<212> TYPE: DNA
<213> ORGANISM: Artificial Sequence
<220> FEATURE:
<223> OTHER INFORMATION: V660A primer

<400> SEQUENCE: 15
ggatccaccg ccacgtggga a                                               21

<210> SEQ ID NO 16
<211> LENGTH: 27
<212> TYPE: DNA
<213> ORGANISM: Artificial Sequence
<220> FEATURE:
<223> OTHER INFORMATION: A231V primer

<400> SEQUENCE: 16
atacgtctag atgttgtaaa acatatg                                         27

<210> SEQ ID NO 17
<211> LENGTH: 27
<212> TYPE: DNA
<213> ORGANISM: Artificial Sequence
<220> FEATURE:
<223> OTHER INFORMATION: A230X primer
<220> FEATURE:
<221> NAME/KEY: misc_feature
<222> LOCATION: (13)..(14)
<223> OTHER INFORMATION: N is A, T, C or G
```

```
<220> FEATURE:
<221> NAME/KEY: misc_feature
<222> LOCATION: (15)..(15)
<223> OTHER INFORMATION: S is G or C

<400> SEQUENCE: 17
atccgcatgg atnnsgtgaa gcatatg                                      27
```

US 7,803,598 B2

CYCLODEXTRIN GLYCOSYLTRANSFERASE (CGTASE) POLYPEPTIDES WITH MODIFIED HYDROLYSIS ACTIVITY

REFERENCE TO RELATED APPLICATIONS

This application is a continuation-in-part of international application PCT/IB2004/001136 filed Mar. 8, 2004, and published as WO 2004/081171 on Sep. 23, 2004, which claims priority from Great Britain application 0305685.0 filed Mar. 12, 2003.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF THE INVENTION

The present invention relates to variants of enzymes wherein the variants have a modified hydrolysis activity and in particular a modified endo-/exo-amylase activity.

In one aspect, the present invention relates to variants of enzymes wherein the variants have a reduced endo-amylase activity and optionally an increased hydrolysis activity.

In another aspect, the present invention relates to a variant enzyme—in particular cyclodextrin glycosyltransferases—having an increased hydrolysis activity and a reduced endoamylase activity, compared to the reference and/or parent enzyme, wherein said reference and/or parent is a member of the α-amylase family. Sometimes herein cyclodextrin glycosyltransferases are referred to as CGTases.

More in particular the present invention relates to a variant enzyme (in particular CGTases) having an increased hydrolysis activity and a reduced endoamylase activity compared to the reference and/or parent enzyme, wherein said reference and/or parent is a member of the α-amylase family 13.

TECHNICAL BACKGROUND AND PRIOR ART

The α-amylase family, or glycoside hydrolase family 13 (Henrissat, B. and Davies, G. (1997) *Curr. Opin. Struct. Biol.* 7, 637-644), is a large family of starch processing enzymes. The (β/α)$_8$-barrel fold of the catalytic domain, the catalytic site residues and the α-retaining bond cleavage mechanism are conserved in this family (McCarter, J. D. and Withers, S. G. (1994) *Curr. Opin. Struct. Biol.* 4, 885-892; Uitdehaag, J. C. M., et al., (1999) *Nature Struct. Biol.* 6, 432436), but the product and reaction specificity vary widely (Kuriki, T. and Imanaka, T. (1999) *J. Biosci. Bioeng.* 87, 557-565).

The α-amylase family 13 includes enzymes such as cyclodextrin glycosyltransferase—also known as cyclomaltodextrin glucanotransferase or cyclodextrin glucanotransferase (GGTase EC 2.4.1.19) and α-amylases (EC 3.2.1). CGTase and α-amylase are two classes of glycosylases that degrade starch by hydrolysis of α-(1,4)-glycosidic bonds, but the initial break down products are predominantly cyclic oligosaccharides for CGTases (also called cyclodextrins) and linear oligosaccharides for the α-amylases.

CGTases can catalyse the breakdown of starch and similar substances into cyclodextrins via an intramolecular transglycosylation reaction, thereby forming circular α(1,4)-linked oligosaccharides of varying sizes called cyclodextrins (also referred to as CDs). The circular α-(1,4)-linked oligosaccharides (cyclodextrins) are formed from linear α-(1,4)-linked oligosaccharide substrates.

The CGTase enzyme consists of five domains (A-E); domains A and B constitute the catalytic domains, domain E is involved in raw starch binding (Penninga, D., et al., (1996) *J. Biol. Chem.* 271, 32777-32784; Ohdan, K., et al. (2000) *Appl. Environ. Microbiol.* 66, 3058-3064), while the functions of domains C and D are not known yet. After binding of the substrate across several sugar binding subsites (labelled −7 to +2; FIG. 1), the α-(1,4)-glycosidic bond between subsites −1 and +1 is cleaved to yield a covalent glycosyl-enzyme intermediate that is bound at the donor subsites (−1, −2, −3, etc.) (Uitdehaag, J. C. et al., (1999) *Nature Struct. Biol.* 6, 432-436). In the next step of the reaction an acceptor molecule binds at acceptor subsite +1 and cleaves the glycosyl-enzyme bond.

In the cyclization reaction the non-reducing end of the covalently bound sugar is used as the acceptor to yield a cyclodextrin. At a very low rate, CGTase may also use water or a second sugar molecule as acceptor, which results in a hydrolysis or a disproportionation reaction, respectively, thus forming linear oligosaccharides.

While α-amylase is a strongly hydrolytic enzyme, CGTase is first of all a transglycosylase. The hydrolitic activity of CGTase is generally much lower than the transglycosylation activity. It has been reported that CGTases from *Thermoanaerobacter* and *Thermoanaerobacterium thermosulfurigenes* strain EM1 (*Tabium*) have relatively high hydrolysis activity, although still considerably lower than compared to α-amylases (Norman and Jorgensen, 1992, *Denpun Kagaku*, 39: 101-108; Wind et al., 1995, *Appl. Environm. Microbiol.* 61: 1257-1265).

It has been suggested that the relative efficiencies of the hydrolysis and transglycosylation reactions of the CGTase enzyme are determined by the nature of the acceptor used in the second half of the reaction and thus by the properties of the acceptor subsites. In respect of this, van der Veen and colleagues have reported that CGTase has a clear preference for glucosyl acceptors, as its transglycosylation activities are much higher than the hydrolysis activity (van der Veen, B. A., et al., (2000) *Eur. J. Biochem.* 267, 658-665). In this respect, Nakamura et al., report that +2 substrate binding subsite, which contains a conserved Phe184 and Phe260 residues is important for the transglycosylation activity (Nakamura et al., 1994, *Biochemistry*, 33: 9926-9936). Furthermore, Leemhuis et al., have reported that the amino acid side chain at position 260 also controls the hydrolytic activity of CGTases (Leemhius et al., 2002, *FEBS letters* 514: 189-192). Moreover, they have reported that mutating Phe260 can change CGTase from transglycosylase to a starch hydrolase.

U.S. Pat. No. 6,482,622, discloses that a maltogenic alpha-amylase from *Bacillus*, commercially available under the trade name Novamyl®, shares several characteristics with CGTases, including sequence homology and formation of transglycosylation products. CGTase variants are described that have the ability to form linear oligosaccharides when acting on starch.

SUMMARY OF THE PRESENT INVENTION

The present invention provides novel variants of enzymes, as well as nucleotide sequences for same and embodiments either comprising or using same, that belong to the α-amylase family of enzymes. The variants have useful activities.

CGTase Numbering

In the context of the present invention a specific numbering of amino acid residue positions in CGTase enzymes is employed.

In this respects by alignment of the amino acid sequences of various known CGTases it is possible to unambiguously allot a CGTase amino acid position number to any amino acid residue position in any CGTase enzyme, the amino acid sequence of which is known.

Using this numbering system originating from for example the amino acid sequence of the CGTase obtained from *Bacillus circulans* strain 251, aligned with amino acid sequences of a number of other known CGTases, it is possible to indicate the position of an amino acid residue in a CGTase unambiguously.

This CGTase numbering system has been described in WO 96/33267, Table 1, page 8-31 (*Bacillus circulans* strain 251 is represented as a). Table 1 of WO 96/33267 also shows protein sequences of a number of relevant CGTases and is hereby incorporated by reference.

In describing the different CGTase radiants produced or which are contemplated to be encompassed by the present invention, the following nomenclature will be adopted for ease of reference:

[original amino acid/position according to the numbering system/substituted amino acid]

Accordingly, the substitution of alanine with valine in position 230 is designated as A230V.

Multiple mutations are separated by slash marks "/", e.g. A230V/T514A representing mutations in position 230 and 514 substituting alanine with valine and threonine with alanine respectively.

All positions referred to in the present application by CGTase numbering refer to the *Bacillus circulans* CGTase numbering described herein.

The numbering system, even though it may use a specific sequence as a base reference point, is also applicable to all relevant homologous sequences. Sequence homology between proteins may be ascertained using well known alignment programs and hybridisation techniques described herein.

In some aspects of the present invention there is just one mutation. In other aspects of the present invention there are two mutations. In other aspects of the present invention there are three mutations. In other aspects of the present invention there are more than three mutations.

Broad Aspects of the Present Invention

Whereas exo-amylases like amyloglucosidase and beta-amylase are totally exo-specific in that they virtually always cleave the substrate (e.g. starch) from the non-reducing end and thus have no endo-activity, other amylases—such as maltogenic alpha-amylase—can cleave starch internally and thus have a varying degree of exo-specificity.

In one broad aspect, present invention relates to a variant enzyme having an increased exo-specificity.

Exo-specificity is measured as the ratio of total hydrolytic activity to endo-activity. It follows that a variant with increased exo-specificity would either have increased total hydrolytic activity and/or decreased endo-activity.

In another broad aspect, the present invention provides variant α-amylase family enzymes which when compared to the reference and/or parent enzymes under the same conditions, show increased hydrolase activity and/ore reduced endo-activity.

In a further broad aspect, the present invention provides variant α-amylase family members—for example variant CGTases or variant maltogenic alpha-amylases—that have an increased exo-specificity when compared to the reference and/or parent enzymes.

The present invention also provides nucleic acid sequences coding for the polypeptides according to the present invention.

Also provided is a vector comprising the nucleic acid sequences of the present invention, operably linked to a regulatory sequence capable of regulating the expression of said nucleotide sequences in a suitable host cell.

A host cell comprising a nucleic acid or a vector of the invention is also provided.

In another aspect, the present invention provides a method of making the polypeptides of the invention comprising transforming a host cell with a nucleic acid encoding the desired polypeptide, culturing the transformed cell, expressing said polypeptide, optionally purifying and/or isolating said polypeptide and optionally testing the polypeptide for the desired activity.

Our results demonstrate that these variant polypeptides have improved properties that make them suitable for a variety of applications such as baking.

Also provided is the use of the variant polypeptides of the invention in baking.

Also provided is a process of treating starch comprising contacting the starch with a variant enzyme according to the present invention and allowing the enzyme to generate from the starch one or more linear substrates and optionally isolating and/or purifying same.

Specific Aspects of the Present Invention

Some specific aspects of the present invention are presented in the accompanying claims.

For example, according to one aspect of the present invention there is provided:

an isolated and/or purified enzyme variant comprising one or more amino acid modifications at one, or more of the following positions (using *Bacillus circulans* CGTase numbering) relative to a reference enzyme:
Position 230
Position 8
Position 21
Position 47
Position 94
Position 215

Position 232
Position 245
Position 259
Position 263
Position 299
Position 320
Position 357
Position 514
Position 633
Position 655
Position 660
Position 672;
or equivalent position(s) in other homologous members of the α-amylase family;
wherein said enzyme variant has a higher hydrolase activity on incubation with starch when compared to the reference enzyme under the same conditions,
wherein said reference enzyme is a member of the α-amylase family.

The reference enzyme does not have one or more corresponding amino acid modifications. Preferably, the reference enzyme does not have all of the corresponding amino acid modifications (i.e. all of modifications of the variant).

Alternatively expressed, according to one aspect of the present invention there is provided:
an isolated and/or purified enzyme variant that differs by one or more amino acid modifications at one or more of the following positions (using *Bacillus circulans* CGTase numbering):
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672;
or equivalent position(s) in other homologous members of the α-amylase family;
to a reference sequence;
and wherein said enzyme variant has a higher hydrolase activity on incubation with starch when compared to the reference enzyme under the same conditions;
wherein said reference enzyme is a member of the α-amylase family.

The reference enzyme does not have one or more corresponding amino acid modifications. Preferably, the reference enzyme does not have all of the corresponding amino acid modifications. (i.e. all of modifications of the variant).

The enzyme variant may occur in nature. Alternatively, the enzyme variant may be prepared de novo or it may be prepared by modifying a reference and/or parent enzyme.

Thus, according to a further aspect of the present invention there is provided:
an isolated and/or purified enzyme variant derivable from a parent enzyme, which parent enzyme is a member of the α-amylase family,
wherein said enzyme variant comprises one or more amino acid modifications at one or more of the following positions (using *Bacillus circulans* CGTase numbering) relative to the parent enzyme:
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672;
or equivalent position(s) in other homologous members of the α-amylase family,
and wherein said enzyme variant has a higher hydrolase activity on incubation with starch when compared to the parent enzyme under the same conditions.

Another aspect of the present invention relates to:
a method of preparing an enzyme variant; wherein said method comprises expressing a variant nucleotide sequence encoding said enzyme variant; wherein said enzyme variant comprises one or more amino acid modifications at one or more of the following positions (using *Bacillus circulans* CGTase numbering) relative to a reference enzyme:
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672;
or equivalent position(s) in other homologous members of the α-amylase family;
and wherein said enzyme variant has a higher hydrolase activity on incubation with starch when compared to the reference enzyme under the same conditions;
wherein said reference enzyme is a member of the α-amylase family.

The reference enzyme does not have one or more corresponding amino acid modifications. Preferably, the reference enzyme does not have all of the corresponding amino acid modifications (i.e. all of modifications of the variant).

Alternatively expressed, according to one aspect of the present invention there is provided:

a method of preparing an enzyme variant; wherein said method comprises expressing a variant nucleotide sequence encoding said enzyme variant; wherein said enzyme variant differs by one or more amino acid modifications at one or more of the following positions (using Bacillus circulans CGTase numbering):
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672;
or equivalent position(s) in other homologous members of the α-amylase family;
to a reference sequence;
and wherein said enzyme variant has a higher hydrolase activity on incubation with starch when compared to the reference enzyme under the same conditions;
wherein said reference enzyme is a member of the α-amylase family.

The reference enzyme does not have one or more corresponding amino acid modifications. Preferably, the reference enzyme does not have all of the corresponding amino acid modifications. (i.e. all of modifications of the variant).

The variant nucleotide sequence may occur in nature. Alternatively, the variant nucleotide sequence may be prepared de novo or it may be prepared by modifying a parent nucleotide sequence enzyme.

Thus, according to a further aspect of the present invention there is provided:
a method of preparing an enzyme variant; wherein said method comprises expressing a variant nucleotide sequence encoding said enzyme variant; wherein said variant nucleotide sequence is obtainable by mutating a parent nucleotide sequence, wherein said parent nucleotide sequence encodes for a parent enzyme; wherein the parent enzyme is a member of the α-amylase family; and wherein said enzyme variant has a higher hydrolase activity on incubation with starch when compared to the parent enzyme under the same conditions; and wherein said enzyme variant comprises one or more amino acid modifications at one or more of the following positions (using Bacillus circulans CGTase numbering) relative to the parent enzyme:
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672;
or their equivalent positions in other homologous members of the α-amylase family.

According to another aspect of the present invention there is provided:
a method of preparing an enzyme variant; said method comprising expressing variant nucleotide sequence encoding said enzyme variant; wherein said variant nucleotide sequence is obtained from mutating a reference nucleotide sequence, wherein said reference nucleotide sequence encodes for a reference enzyme; wherein the reference enzyme is a member of the α-amylase family; and wherein said enzyme variant has a lower hydrolase activity on incubation with starch when compared to the reference enzyme under the same conditions; and wherein said enzyme variant comprises one or more amino acid modifications at one or more of the following positions (using Bacillus circulans CGTase numbering) relative to the reference enzyme:
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672
or equivalent position(s) in other homologous members of the α-amylase family;
and wherein said enzyme variant has a higher hydrolase activity on incubation with starch when compared to the reference enzyme under the same conditions;
wherein said reference enzyme is a member of the α-amylase family.

The reference enzyme does not have one or more corresponding amino acid modifications. Preferably, the reference enzyme does not have all of the corresponding amino acid modifications (i.e. all of modifications of the variant).

Alternatively expressed, according to one aspect of the present invention there is provided:
a method of preparing an enzyme variant; said method comprising expressing a variant nucleotide sequence encoding said enzyme variant; wherein said variant nucleotide sequence is obtained from mutating a reference nucleotide sequence, wherein said reference nucleotide sequence encodes for a reference enzyme; wherein the reference enzyme is a member of the α-amylase family; and wherein said enzyme variant has a lower hydrolase activity on incubation with starch when compared to the reference enzyme under the same conditions; and wherein said enzyme variant differs by one or more amino acid modifications at one or more of the following positions (using *Bacillus circulans* CGTase numbering):
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672
or equivalent position(s) in other homologous members of the α-amylase family,
to the reference sequence;
and wherein said enzyme variant has a higher hydrolase activity on incubation with starch when compared to the reference enzyme under the same conditions;
wherein said reference enzyme is a member of the α-amylase family.

The reference enzyme does not have one or more corresponding amino acid modifications. Preferably, the reference enzyme does not have all of the corresponding amino acid modifications (i.e. all of modifications of the variant).

The variant nucleotide sequence may occur in nature. Alternatively, the variant nucleotide sequence may be prepared de nova or it may be prepared by modifying a parent nucleotide sequence enzyme.

Thus, according to a further aspect of the present invention there is provided:
  a method of preparing an enzyme variant; said method comprising expressing a variant nucleotide sequence encoding said enzyme variant; wherein said variant nucleotide sequence is obtained from mutating a parent nucleotide sequence, wherein said parent nucleotide sequence encodes for a parent enzyme; wherein the parent enzyme is a member of the α-amylase family; and wherein said enzyme variant has a lower hydrolase activity on incubation with starch when compared to the parent enzyme under the same conditions; and wherein said enzyme variant comprises one or more amino acid modifications at one or more of the following positions (using *Bacillus circulans* CGTase numbering relative to the parent enzyme:
Position 230
Position 8
Position 21
Position 47
Position 94
Position 215
Position 232
Position 245
Position 259
Position 263
Position 299
Position 320
Position 357
Position 514
Position 633
Position 655
Position 660
Position 672;
or their equivalent positions in other homologous members of the α-amylase family.

Reference Enzyme

The term "reference enzyme" as used herein means the enzyme that has a close, preferably the closest, chemical structure to the resultant variant. The reference enzyme may be a precursor enzyme (i.e. the enzyme that is actually mutated) or it may be prepared de novo. The reference enzyme may be a wild type enzyme.

The term "precursor" as used herein means an enzyme that precedes the enzyme which is modified according to method of the present invention. Thus, the precursor may be an enzyme that is modified by mutagenesis according to the present invention. Likewise, the precursor may be a wild type enzyme, a variant wild type enzyme or an already mutated enzyme.

The term "wild type" is a term of the art understood by skilled persons and means a phenotype that is characteristic of most of the members of a species occurring naturally and contrasting with the phenotype of a mutant. Thus, in the present context, the wild type enzyme is a form of the enzyme naturally found in most members of the relevant species. Generally, the relevant wild type enzyme in relation to the variant polypeptides of the invention is the most closely related corresponding wild type enzyme in terms of sequence homology.

However, where a particular wild type sequence has been used as the basis for producing a variant polypeptide of the invention, this will be the corresponding wild type sequence regardless of the existence of another wild type sequence that is more closely related in terms of amino acid sequence homology.

In the context of the specific aspects of the present invention, examples of reference enzymes include the wild type *Bacillus circulans* strain 251, *Thermoanaerobacterium thermosulfurigenes* strain (*Tabium*) or Novamyl® sequences as shown in SEQ ID 4, SEQ ID 5 or SEQ ID 6 or FIG. 5.

Reference Nucleotide Sequence

The term "reference nucleotide sequence" as used herein means a sequence that encodes for the reference enzyme.

Parent Enzyme

The term "parent enzyme" as used herein means the enzyme that has a close, preferably the closest chemical structure to the resultant variant. The parent enzyme is typically a precursor enzyme (i.e. the enzyme that is actually mutated) or it may be prepared de novo. The parent enzyme may be a wild type enzyme.

The term "precursor" as used herein means an enzyme that precedes the enzyme which is modified according to method of the present invention. Thus, the precursor may be an enzyme that is modified by mutagenesis according to the present invention. Likewise, the precursor may be a wild type enzyme, a variant wild type enzyme or an already mutated enzyme.

The term "wild type" is a term of the art understood by skilled persons and means a phenotype that is characteristic of most of the members of a species occurring naturally and contrasting with the phenotype of a mutant. Thus, in the present context, the wild type enzyme is a form of the enzyme naturally found in most members of the relevant species. Generally, the relevant wild type enzyme in relation to the variant polypeptides of the invention is the most closely related corresponding wild type enzyme in terms of sequence homology.

However, where a particular wild type sequence has been used as the basis for producing a variant polypeptide of the invention, this will be the corresponding wild type sequence regardless of the existence of another wild type sequence that is more closely related in terms of amino acid sequence homology.

In the context of the specific aspects of the present invention, examples of parent enzymes include the wild type *Bacillus circulans* strain 251, *Thermoanaerobacterium thermosulfurigenes* strain (*Tabium*) or Novamyl® sequences as shown in SEQ ID 4, SEQ ID 5 or SEQ ID 6 or FIG. 5.

Parent Nucleotide Sequence

The term "parent nucleotide sequence" as used herein means a sequence that encodes for the parent enzyme.

Preferable Aspects of the Present Invention

Preferable aspects of the present invention are presented herein and in the claims.

Specific Preferable Aspects of the Present Invention

In a specific preferred embodiment, the present invention provides a variant CGTase polypeptide having an increased hydrolase activity and reduced endo-amylase activity as compared to the reference and/or parent enzyme, comprising one or more amino acid modifications when compared to (i.e. relative to) the reference and/or parent enzyme.

In another specific preferred embodiment, the present invention provides a variant CGTase polypeptide having an increased hydrolase activity and/or reduced endo-amylase activity which is derived from a reference and/or parent CGTase such that the variant CGTase incorporates at any one or more of amino acid residues numbers as listed herein or as shown in SEQ ID No 4 of the *B. circulans* strain 251 or their equivalent positions in other homologous CGTase polypeptides (see FIG. 5).

In yet another preferred embodiment, the present invention provides a variant maltogenic α-amylase enzyme Novamyl® having altered starch hydrolase activity and an altered endo-amylase activity compared to the reference and/or parent enzyme, comprising one or more amino acid modifications at any one of amino acid residues numbers listed herein or as shown in SEQ ID No. 6 of the Novamyl® enzyme or their equivalent positions in other homologous maltogenic α-amylase polypeptides. The reference and/or parent maltogenic α-amylase enzyme Novamyl® was isolated from *Bacillus* sp., EP 120 693) and is a commercially available product of Novo Nordisk A/S, Denmark).

Preferably, the modifications are amino acid substitutions.

Preferably, these substitutions are selected from amino acids A230V, F21L, R47L, R47W, N94S, K232L, A245T, F259E, F259I, E264A, A357T, Y633A using *Bacillus circulans* CGTase numbering and their equivalents in other homologous polypeptides.

Preferably, these substitutions are multiple substitutions comprising amino acid A230V in combination with one or more of F21L, R47L, R47W, N94S, K232L, A245T, F259E, F259I, E264A, A357T, Y633A using *Bacillus circulans* CGTase numbering and their equivalents in other homologous polypeptides.

Preferably, the substitutions comprise a combination of amino acid A230V with F259I (i.e. A230V/F259I), using *Bacillus circulans* CGTase numbering and their equivalents in other homologous polypeptides.

General Aspects of the Present Invention

We designed and tested different α-amylase family members using mutagenesis techniques—such as random mutagenesis techniques—to demonstrate that enzymes can be generated that have an increased starch hydrolase activity and reduced endo-amylase activity.

Thus, in a specific aspect of the present invention, and by using mutagenesis techniques we have managed to convert α-amylase family members from endoamylases to exo-acting enzymes.

In particular we have identified a number of specific ammo acid residues, in Family 13 α-amylases that can influence the degree of endospecificity conversion.

By the term "endospecificity conversion" we mean a complete or partial change in the biochemical properties of the Family 13 amylase variant for example a predominantly endo-amylase activity reference and/or parent enzyme is completely or partially induced to act as an exo-acting enzyme. Testing the biochemical properties of the variants according to the present invention can be carried out as described in the Examples.

As a highly preferred aspect, the present invention provides enzyme variants of the α-amylase family comprising one or more amino acid modifications at one or more of the following positions (using *Bacillus circulans* CGTase numbering): 230 and optionally at one or more of: 21, 47, 94, 232, 245, 259, 264, 357, or 633 or their equivalent positions in other homologous members of the α-amylase family. The present invention also provides a polynucleotide sequence coding for same variants.

In yet another more highly preferred aspect, the present invention provides a maltogenic α amylase variant derived from a reference and/or parent maltogenic α-amylase enzyme (Novamyl®) comprising one or more amino acid modifications at one or more of the following positions (using *Bacillus circulans* CGTase numbering): 230 and optionally at one or more of 21, 47, 94, 232, 245, 259, 264, 357, or 633 or their equivalent positions in other homologous enzymes. The present invention also provides a polynucleotide sequence coding for same variants.

In yet another more preferred aspect, the present invention provides a maltogenic α-amylase variant derived from a reference and/or parent maltogenic α-amylase enzyme (Novamyl®) comprising a modification at amino acid 230 in combination with one or more of amino acids: 21, 47, 94, 232, 245, 259, 264, 357; or 633 using the numbering of the *Bacillus circulans* strain 251 or their equivalents in other homologous polypeptides. The present invention also provides a polynucleotide sequence coding for same variants.

In yet another more preferred aspect, the present invention provides a maltogenic α-amylase variant derived from a reference and/or parent maltogenic α-amylase enzyme. (Novamyl®, SEQ ID 6) comprising a modification at amino acid 230 in combination with amino acid 259 (i.e. 230/259), using Bacillus circulans CGTase numbering and their equivalents in other homologous polypeptides. The present invention also provides a polynucleotide sequence coding for same variants.

The α-Amylase Family

The α-amylase family covers more than 27 different enzyme specificities from hydrolases (EC 3), transferases (EC 2) and isomerases (EC 5). They belong to three glycoside hydrolase families 13, 71 and 77, forming a clan GH-H based on such properties as the over amino acid sequence homology and particularly the catalytic site, the three dimensional structural similarities and the geometry of the catalytic site (McCarter, J. D. and Withers, S. G. (1994) *Curr. Opin. Struct. Biol.* 4, 885-892; Uitdehaag, J. C. M., et al., (1999) *Nature Struct. Biol.* 6, 432-436). The α-amylase family members have been reported from nearly 100 different organisms among others fungi and bacteria.

It is intended that the term "α-amylase family" as used herein refers to the α-amylase protein family which as stated herein includes different classes of enzymes such as hydrolases, transferases, isomerase and also proteins (see Table and herein). The above term should be distinguished from the term "α-amylase" which refers to a particular class of enzymes belonging to the α-amylase family of enzymes, namely the hydrolase class.

Of particular interest in respect of the present invention are the enzymes classified in Family 13. This family of enzymes includes among other the enzyme class of transferases for example cyclodextrin glycosyltransferase (CGTase) and the class of hydrolases for example maltogenic α-amylase (See Table A).

TABLE A

The α-amylase protein family.

| Enzyme class | Enzyme name | EC number | GH family |
|---|---|---|---|
| Hydrolases | α-Amylase | 3.2.1.1 | 13 |
| | Oligio-1, 6-glucsidase | 3.2.1.10 | 13 |
| | α-Glucosidase | 3.2.1.20 | 13 |
| | Pullulanase | 3.2.1.41 | 13 |
| | Amylopullulanase | 3.2.1.1/41 | 13 |
| | Cyclomaltodextrinase | 3.2.1.54 | 13 |
| | Maltotetraohydrolase | 3.2.1.60 | 13 |
| | Isoamylase | 3.2.1.68 | 13 |
| | Dextran glucosidase | 3.2.1.70 | 13 |
| | Trehalose-6-phosphate hydrolase | 3.2.1.93 | 13 |
| | Maltohexaohydrolase | 3.2.1.98 | 13 |
| | Maltotriohydrolase | 3.2.1.116 | 13 |
| | Maltogenic amylase | 3.2.1.133 | 13 |
| | Neopullulanase | 3.2.1.135 | 13 |
| | Maltooligosyltrchalose hydrolase | 3.2.1.141 | 13 |
| | Maltopentaohydrolase | 3.2.1.— | 13 |
| Transferases | Amylosucrase | 2.4.1.4 | 13 |
| | Glucosyltransferase | 2.4.1.5 | 70 |
| | Sucrose phosphorylase | 2.4.1.7 | 13 |
| | Glucan branching enzyme | 2.4.1.18 | 13 |
| | Cyclodextrin glucanotransferase (CGTase) | 2.4.1.19 | 13 |
| | Amylomaltase (4-α-Glucanotransferase) | 2.4.1.25 | 13, 77 |
| | Glucan debranching enzyme | 2.4.1.25/3.2.1.33 | 13 |
| | Alternansucrase | 2.4.1.140 | 70 |
| | Maltosyltransferase | 2.4.1.— | 13 |
| Isomerases | Maltooligosyltrehalose synthase Trehalose synthase | — | 13 |
| Proteins | Amino acid transport proteins 4F2 Heavy-chain antigens | — | 13 |

CGTases

In a highly preferred aspect, the reference and/or parent CGTase used in the present invention is all enzyme classified in EC 2.4.1.19. It may be derived from any source, for instance from a bacterial source that may include but is not limited to *Bacillus, Thermoanaerobacter, Klebsiella, Corynebacterium, Brevibacterium, Clostridium, Micrococcus* and *Thermoanaerobacterium*.

The reference and/or parent CGTase preferably has one or more of the following characteristics.
  i) the amino acid has at least 50, preferably at least 60, preferably at least 70, preferably at least 80 preferably at least 90, preferably at least 95, preferably at least 98, preferably at least 99% sequence identity to SEQ ID No 4 or 5;
  ii) it is encoded by a nucleotide sequence which hybridises at conditions described herein to the nucleotide sequence according to SEQ ID 4 or 5 encoding CGTases carried by *B. circulans* strain 251 or *Thermoanaerobacterium thermosulfurigenes* strain (*Tabium*) respectively;
  iii) it has a clear preference for glucosyl acceptors and its transglycosylase activity is much higher than its hydrolase activity.
  iv) its end-amylase activity is much higher than its exo-amylase activity.

Maltogenic α-Amylase

The reference and/or parent maltogenic α-amylase that may be used in the present invention is an enzyme classified in EC 3.2.1.133. The catalytic activity of the enzyme requires a non-reducing end on the substrate and the primary enzymatic activity results in the degradation of amylopectin and amylose to maltose and other linear maltodextrins. This enzyme is also able to hydrolyse amylose and amylopectin to maltose in the α-configuration. Furthermore, at low levels this enzyme is also able to hydrolyse maltotriose as well as cyclodextrins.

A preferred reference and/or parent maltogenic α-amylase which may be used in the present invention is the amylase cloned from *Bacillus* sp. as described in EP 120 693 (commercially known as Novamyl®). Novamyl® has the amino acid sequence set out in SEQ ID 6 and is encoded by the *Bacillus* sp stain NCIB 11837.

Endo-Amylase

By the term "endo-amylase" we mean enzymes that possess a significant capacity to break down starch from the reducing end i.e. internally. However, the enzyme need not just have that activity alone and it may possess other activities. Typically, the other activity will include a significant glycosyltransferase activity and/or hydrolase activity and/or exo-amylase activity. Preferably the exo-amylase activity, if present, is less—preferably much less—than the glycosyltransferase activity and/or hydrolase activity.

Exo-Amylase

By the term "exo-amylase" we mean enzymes that possess a significant capacity to break down starch from the non-reducing end, i.e. the end of the molecule. However, the enzyme need not just have that activity alone and it may possess other activities. Typically, the other activity will include a significant glycosyltransferase activity and/or hydrolysis and/or endo-amylase activity. Preferably the endo-amylase activity, if present, is less—preferably much less—than the glycosyltransferase activity and/or the hydrolase activity.

Hydrolase

By the term "hydrolase" we mean enzymes that possess a significant starch hydrolase activity. However, the enzyme need not just have that activity alone and it may possess other activities. Typically, the other activity will not include a significant glycosyltransferase activity. Preferably the glycosyltransferase activity, if present, is less—preferably much less—than the hydrolase activity.

Glycosyltransferase

By the term "glycosyltransferase" we mean enzymes that possess a significant starch glycosyltransferase activity. However, the enzyme need not just have that activity alone and it may possess other activities. Typically, the other activity will not include a significant hydrolase activity. Preferably the hydrolase activity, if present, is less—preferably much less—than the glycosyltransferase activity.

Amino Acids

In the context of the present invention the following symbols and abbreviations for amino acid residues are used.

| | | |
|---|---|---|
| A | Ala | Alanine |
| B | Ast | Aspartate |
| C | Cys | Cysteine |
| D | Asp | Aspartin acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Aspargine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophane |
| Y | Tyr | Tyrosine |
| Z | Gln | Glutamate |
| X | is any non-aromatic amino acid i.e. not Y, F or W, (unless stated otherwise). | |

Amino Acid Sequences

The present invention also encompasses amino acid sequences of variant enzymes having the specific properties as defined herein.

As used herein, the term "amino acid sequence" is synonymous with the term "polypeptide". and/or the term "protein". In some instances, the term "amino acid sequence" is synonymous with the term "peptide". In some instances, the term "amino acid sequence" is synonymous with the term "enzyme".

The amino acid sequence of the present invention may be prepared and/or isolated from a suitable source, or it may be made synthetically or it may be prepared by use of recombinant DNA techniques.

The variant enzymes of the present invention may be used in conjunction with other enzymes. Thus the present invention also covers a combination of enzymes wherein the combination comprises the variant enzyme of the present invention and another enzyme, which may be another enzyme according to the present invention. This aspect is discussed in a later section.

Preferably the variant enzyme is not a native enzyme. In this regard, the term "native enzyme" means an entire enzyme that is in its native environment and when it has been expressed by its native nucleotide sequence.

Variants

The present invention provides novel α-amylase family variant polypeptides i.e. α-amylase family variants having amino acid sequence not found in nature. Formally, the α-amylase family variants of the present invention may be regarded as a functional derivative of a reference and/or parent α-amylase family enzyme (as defined herein), obtained by substitution, insertion and/or deletion of one or more amino acid residue(s) of the reference and/or parent enzyme. Modification of polypeptide sequences can be carried out using standard techniques such as for example site directed mutagenesis and error-prone polymerase chain reaction (PCR) mutagenesis.

In the context of the present invention, an α-amylase family variant of increased hydrolysis activity and reduced endoamylase activity is an α-amylase family variant capable of producing an increased level of linear oligosaccharides, when compared to the reference and/or parent enzyme.

In an α-amylase family variant of the present invention, one or more amino acid residues corresponding to the following positions (*Bacillus circulans* CGTase numbering) have been introduced by substitution and/or insertion:

Position 8 wherein said mutation is to any of: 8C; 8D; 8F; 8I; 8N; 8P; 8S; 8W or 8Y
Position 21 wherein said mutation is to any of 21A; 21D; 221F; 21L; 21T; 21V; 21W or 21Y
Position 47 wherein said mutation is to any of: 47A; 47C; 47D; 47E; 47F; 47G; 47I; 47K; 47Q, 47L, 47N; 47P; 47R; 47S; 47T; 47V or 47W
Position 94 wherein said mutation is to any of: 94N; or 94S
Position 215 wherein said mutation is to any of: 215I; or 215V
Position 236 wherein said mutation is to any of: 230A; 230C; 230D; 230E; 230F; 230G; 230H; 230I; 230K; 230L; 230M; 230N; 230P; 230Q; 230R; 230S; 230T; 230V; 230W or 230Y
Position 232 wherein said mutation is to any of: 232L
Position 245 wherein said mutation is to any of: 245A; or 245T
Position 259 wherein said mutation is to any of: 259A; 259E; 259F; 259I; or 259S
Position 263 wherein said mutation is to any of: 264A
Position 299 wherein said mutation is to any of: 299D
Position 320 wherein said mutation is to any of: 320Q; or 320L
Position 357 wherein said mutation is to any of: 357A; or 357T
Position 514 wherein said mutation is to any of: 514A.
Position 633 wherein said mutation is to any of: 633A
Position 655 wherein said mutation is to any of: 655K; or 65E
Position 660 wherein said mutation is to any of: 660A; or 660V and/or
Position 672 wherein said mutation is to any of: 672A; or 672G.

In a more preferred α-amylase family variant of the present invention, one or more amino acid residues corresponding to the following positions (Bacillus circulans CGTase numbering) have been introduced by substitution and/or insertion:

Position 8 wherein said mutation is to 8S
Position 21 wherein said mutation is to 21L
Position 47 wherein said mutation is to any of 47Q, 47L, or 47W
Position 94 wherein said mutation is to 94S
Position 215 wherein said mutation is to 215V
Position 230 wherein said mutation is to 230V
Position 232 wherein said mutation is to 232L
Position 245 wherein said mutation is to 245T
Position 259 wherein said mutation is to any of: 259E; 259I; or 259S
Position 263 wherein said mutation is to 264A
Position 299 wherein said mutation is to 299D
Position 320 wherein said mutation is to 320L
Position 357 wherein said mutation is to 357T
Position 514 wherein said mutation is to 514A
Position 633 wherein said mutation is to 633A
Position 655 wherein said mutation is to 655E
Position 660 wherein said mutation is to 660A
Position 672 wherein said mutation is to 672G.

In preferred embodiment the variant α-amylase family enzyme is a variant maltogenic α-amylase enzyme. Accordingly, the present invention provides a variant maltogenic α-amylase polypeptide having increased starch hydrolase activity and/or reduced endo-amylase activity compared to the reference and/or parent enzyme, in which one or more amino acid modifications have been introduced by substitution and/or insertion.

Preferably the maltogenic α-amylase variant is derived from *Bacillus* strain NCIB 11837, as shown in SEQ ID 6 or homologues thereof.

The α-amylase family variant of the present invention may be derived from any α-amylase family member enzyme found in nature.

Preferably the α-amylase sequence to be modified is that of a Family 13 α-amylase enzyme, more preferably a Family 13 α-amylase from a strain of *Bacillus*, a strain of *Thermoanaerobacter*, a strain of *Klebsiella*, a strain of *Corynebacterium*, a strain of *Brevibacterium*, a strain of *Clostridium*, a strain of *Micrococcus* or a strain of *Thermoanaerobacterium*.

In a more preferred embodiment, the α-amylase variant of the present invention is derived from a strain of *Bacillus autolyticus*, a strain of *Bacillus cereus*, a strain of *Bacillus circulans*, a strain of *Bacillus circulans* var. *alkalophilus*, a strain of *Bacillus coagulans*, a strain of *Bacillus firmus*, a strain of *Bacillus halophilus*, as strain of *Bacillus macerans*, a strain of *Bacillus megaterium*, a strain of *Bacillus ohbensis*, a strain of *Bacillus stearothermophilus*, a strain of *Bacillus subtilis*, a strain of *Klebsiella pneumonia*, a strain of *Thermoanaerobacter ethanolicus*, a strain of *Thermoanaerobacter finni*, a strain of *Clostridium thermoamylolyticum*, a strain of *Clostridium thermosaccharolyticul*, or a strain of *Thermoanaerobacterium thermosulfurigenes*.

If the CGTase variant of the present invention is derived from a strain of *Bacillus circulans*, one or more amino acid modifications may be introduced by substitution and/or insertion.

Preferably the CGTase variant is derived from *Bacillus circulans* strain 251, as shown in SEQ ID 1 or homologues thereof.

The Examples describe the construction of *Bacillus circulans* strain 251 CGTase variant in which one or more amino acid modifications have been introduced by substitution and/or insertion for example A230V, A230V/F21L, A230V/A245T/A357T, A230V/F21L/N94S, A230V/F21L/R47W.

Preferably the CGTase variant is derived from a *Thermoanaerobacterium thermosulfurigenes* strain EM1 (*Tabium*) as shown in SEQ ID 2 or homologues thereof. The Examples describe the construction of *Thermoanaerobacterium thermosulfurigenes* strain EM1 (*Tabium*) CGTase variants in which one or more amino acid modifications have been introduced by substitution and/or insertion for example A231V, F260E and/or A231V/F260E.

It should be noted that amino acids 231 and 260 of *Thermoanaerobacterium thermosulfurigenes* strain EM1 (*Tabium*) CGTase correspond to amino acids 230 and 259 of *Bacillis circulans* strain 251 respectively (see U.S. Pat. No. 6,482,622 showing sequence alignment of Novamyl® with CGTAse from *Thermoanaerobacterium thermosulfurigenes*, *Bacillus circulans* and *Thermoanaerobacter*, for ease of reference this alignment is reproduced herein as FIG. 5.

Accordingly, the variant CGTases comprising the one or more amino acid residues show increased hydrolytic activity and reduced endoamylase activity in which random mutagenesis has lead to an increase in the level of linear oligosaccharide production relative to CDs when compared to the reference and/or parent CGTase.

Preferably the maltogenic α-amylase variant is derived from *Bacillus* sp. (Novamyl®), as shown in SEQ ID 3 or homologues thereof. The Examples describe the construction of Novamyl® variants in which one or more amino acid modifications have been introduced by substitution and/or insertion, for example A229V, A229V/F16L, A229V/K244T and/or A229V/Y258X (where X is any non-aromatic amino acid i.e. not Y, F or W) (numbering according to Novamyl®).

More preferably the maltogenic α-amylase variant is derived from *Bacillus* sp. (Novamyl®) and comprises a double substitution A229V/Y258X (where X is any non-aromatic amino acid i.e. not Y, F or W) (numbering according to Novamyl®).

It should be noted that amino acids 16, 229, 244 and 259 of Novamyl® correspond to amino acids 21, 230, 245 and 259 of *Bacillis circulans* strain 251 respectively (see U.S. Pat. No. 6,482,622 showing sequence alignment of Novamyl® with CGTAse from *Thermoanaerobacterium thermosulfurigenes*, *Bacillus circulans* and *Thermoanaerobacter*, for ease of reference this alignment is reproduced herein as FIG. 5.

Accordingly, the variant Novamyl® comprising the one or more amino acid residues show altered transglycosylase activity and altered hydrolase activity in which mutagenesis leads to altered levels of CDs and linear products when compared to the reference and/or parent Novamyl®.

Identity and Homology

The present invention encompasses the use of homologues and derivatives of any amino acid sequence of the variant enzymes of the present invention or of any nucleotide sequence encoding such variant enzymes. Here, the term "homologue" means an entity having a certain homology with the amino acid sequences of the variants and the nucleotide sequences of the variants. Here, the term "homology" can be equated with "identity".

In the present context, a homologous sequence is taken to include an amino acid sequence which may be at least 50, 60, 75, 80, 85 or 90% identical, preferably at least 95, 96, 97, 98 or 99% identical to the relevant comparative sequence—such as the sequence of the reference and/or parent. Typically, the homologues will comprise the same active sites etc. as the amino acid sequence of the variant. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "mapped" alignment. Typically, such ungapped alignments are performed only over a relatively short number of residues.

Although this is a very simple and consistent method, it fails to take into consideration that for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affinity gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties.

Preferably, for the purposes of the present invention, the degree of identity may be determined according to the method described in Needleman S. B. and Wunch C. D., (1970), (*Journal of Molecular Biology*, 48: 443-445) with the following settings for polypeptide sequence comparison: GAP creation penalty of 30 and GAP extension penalty of 0.1. The determination may be done by means of known computer programs such as GAP provided in the GCG program package (Program Manual of the Wisconsin Package, Version 8, August 1994, Genetics Computer Group, 575 Science Drive, Madison, Wis., USA 53711).

Examples of other software that can perform sequence comparisons include, but are not limited to the BLAST package (see Ausubel et. al., 1999 *Short Protocols in Molecular Biology*, 4th Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent variant enzyme. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

In particular the variants have an amino acid identity with the reference and/or parent enzymes derived from *B. circulans* strain 251, *Thermoanaerobacterium thermosulfurigenes* strain EM1 (*Tabium*) or the Novamyl® sequences of at least 50, 60, 70%, preferably at least 80% e.g. at least 90% preferably at least 95% or at least 98 or 99% homology over at least 50 or 100 amino acid residues comprising the active site.

Preparation of the Nucleotide Sequence

A nucleotide sequence encoding either an enzyme which has the specific properties as defined herein or an enzyme which is suitable for modification may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme encoding clones from the genomic library prepared from the orgasm. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme, thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al. (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Salki R K et al., (*Science* (1988) 23, pp 487-491).

Mutagenesis

One general approach for modifying proteins and enzymes has been based on random mutagenesis. For instance the random mutagenesis may be performed by use of a suitable physical or chemical mutagenising agents, by use of suitable oligonucleotides or by subjecting the precursor DNA sequence to PCR generated mutagenesis such as error-prone PCR Furthermore, the random mutagenesis may be performed by use of any combination of these mutagenising agents. The mutagenising agent may for example be one which induces insertions, deletions, transitions, transversions, inversions and/or scrambling. Examples of a physical or chemical agents suitable for the present invention include among others ultraviolet (UV) irradiation, hydroxylamine and nucleotide analogues. When such agents are used, the mutagenesis is typically performed by incubating the DNA sequence encoding the reference and/or parent enzyme to be mutagenised in the presence of the mutagenising agent of choice under suitable conditions for the mutagenesis to take place, and selecting for mutated DNA having the desired properties.

When the mutagenesis is performed with the assistance of oligonucleotides, the oligonucleotides may be designed to incorporate one or more non-reference and/or non-parent nucleotides during the synthesis of the oligonucleotide. The purpose of this is to maximise the incorporation of the specific nucleotides thus ensuring the expression of the desired amino acid. These oligonucleotides can be incorporated into the DNA encoding the α-amylase family member of the present invention by any published technique e.g. PCR, LCR or any DNA polymerase and ligase as considered appropriate.

In a further embodiment, the variant polypeptides of the invention may be purified and isolated naturally occurring mutant α-amylase family members. Alternatively, mutant α-amylase family members may be generated by subjecting orgasms to physical and/or chemical mutagens as described herein and then screening for organisms comprising mutations in their α-amylase genes. Naturally occurring mutants and mutants generated by random mutagenesis may be identified/screened using a variety of techniques such as PCR screening using suitable nucleic acid primers to amplify regions of α-amylase family genes and sequencing the resulting fragments.

Thus variant polypeptides of the invention include naturally occurring mutant α-amylase family members (purified and isolated from the organisms in which they occur or obtained recombinantly), mutant α-amylase family members obtained by random mutagenesis and mutant enzymes obtained by site-directed mutagenesis.

Variant polypeptides of the invention may also be subjected to further modifications that do not necessarily affect the ability of the α-amylase family members to act as an exo-amylase.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Polypeptides of the invention also include fragments of the full-length sequences of α-amylase family member which have increase hydrolysis activity and optionally reduced endo-amylase activity Polypeptides of the invention may further comprise heterologous amino acid sequences, typically at the N-terminus or C-terminus, preferably the N-terminus. Heterologous sequence may include sequences that affect intra or extracellular protein targeting (such as leader sequences).

Polypeptides of the invention are typically made by recombinant means, for example as described herein. However they may also be made by synthetic means using techniques well known to skilled persons such as solid phase synthesis. Polypeptides of the invention may also be produced as fusion proteins, for example to aid in extraction and purification. It may also be convenient to include a proteolytic cleavage site between the fusion protein partner and the protein sequence of interest to allow removal of fusion protein sequences, such as a thrombin cleavage site. Preferably the fusion protein will not hinder the function of the protein of interest sequence.

The use of appropriate host cells is expected to provide for such post-translational modifications as may be needed to confer optimal biological activity on recombinant expression products of the invention.

Site-Directed Mutagenesis

Once an enzyme-encoding nucleotide sequence has been isolated, or a putative enzyme-encoding nucleotide sequence has been identified, it may be desirable to mutate the sequence in order to prepare an enzyme of the present invention.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151).

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Polynucleotides

Polynucleotides of the invention comprise nucleic acid sequences encoding the variant polypeptide sequences of the invention.

It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Expression of Enzymes

The nucleotide sequence for use in the present invention may be incorporated into a recombinant replicable vector. The vector may be used to replicate and express the nucleotide sequence, in enzyme form, in and/or from a compatible host cell.

Expression may be controlled using control sequences eg. regulatory sequences.

The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Regulatory Sequences

In some applications, the nucleotide sequence for use in the present invention is operably linked to a regular sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Expression Vector

The term "expression vector" means a construct capable of in vivo or in vitro expression Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described herein to provide for expression of a polypeptide of the present invention.

The choice of vector eg. a plasmid, cosmid, or phage vector will often depend on the host cell into which it is to be introduced.

The vectors for use in the present invention may contain one or more selectable marker genes such as a gene, which confers antibiotic resistance eg. ampicillin, kanamycin, chloramphenicol or tetracyclin resistance. Alternatively, the selection may be accomplished by co-transformation (as described in WO91/17243).

Vectors may be used in vitro, for example for production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Host Cells

The term "host cell"—in relation to the present invention includes any cell that comprises either the nucleotide sequence or an expression vector as described herein and which is used in the recombinant production of an enzyme having the specific properties as defined herein.

Thus, a further embodiment of the present invention provides host cells transformed or transfected with a nucleotide sequence that expresses the enzyme of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the enzyme of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise the nucleotide sequence coding for the enzyme according to the present invention and/or products obtained therefrom, and/or wherein a promoter can allow expression of the nucleotide sequence according to the present invention when present in the organism.

A heterologous host may also be chosen wherein the polypeptide of the invention is produced in a form which is substantially free from other α-amylase family members. This may be achieved by choosing a host which does not normally produce such enzymes.

Suitable organisms may include a prokaryote, fungus, yeast or a plant.

The term "transformed organism" in relation to the present invention includes any organism that comprises the nucleotide sequence coding for the enzyme according to the present invention and/or the products obtained therefrom, and/or wherein a promoter can allow expression of the nucleotide sequence according to the present invention within the organism. Preferably the nucleotide sequence is incorporated in the genome of the organism.

The term "transformed organism" does not cover native nucleotide coding sequences in their natural environment when they are under the control of their native promoter which is also in its natural environment.

Therefore, the transformed organism of the present invention includes an organism comprising any one of, or combinations of, the nucleotide sequence coding for the enzyme according to the present invention, constructs according to the present invention, vectors according to the present invention, plasmids according to the present invention, cells according to the present invention, tissues according to the present invention, or the products thereof.

For example the transformed organism may also comprise the nucleotide sequence coding for the enzyme of the present invention under the control of a heterologous promoter.

Transformation of Host Cells/Organism

As indicated earlier, the host organism can be a prokaryotic or a eukaryotic organism.

Examples of suitable prokaryotic hosts include *E. coli* and *Bacillus subtilis* Bacteria from the genus *Bacillus* may be suitable as heterologous hosts because of their capability to secrete proteins into the culture medium. Other bacteria suitable as hosts are those from the genera *Streptomyces* and *Pseudomonas*. Examples of suitable prokaryotic hosts include the gram positive bacteria such as *Bacillus autolyticus, Bacillus cereus, Bacillus circulans, Bacillus circulans* var. *alkalophilus, Bacillus coagulans, Bacillus firmus, Bacillus halophilus, Bacillus macerans, Bacillus megaterium, Bacillus ohbensis, Bacillus stearothermophilus, Bacillus subtilis, Strepomyces murinus, Strepomyces lividans* or gram negative bacteria such as *E. coli*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et. al., Short Protocols in Molecular Biology (1999), 4$^{th}$ Ed., John Wiley & Sons, Inc.

If a prokaryotic host is used then the nucleotide sequence may need to be suitably modified before transformation—such as by removal of introns. In some instances, preferably the organism is a bacterium of the genus *Bacillus* sp. or *Thermoanaerobacterium*, more preferably *Bacillus circulans* or *Thermoanaerobacterium thermosulfurigenes*.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Examples of fungal expression hosts within the scope of the present invention are *Aspergillus* species and *Trichoderma* species; bacteria such as *Bacillus* species, *Streptomyces* species and *Pseudomonas* species; and yeasts such as *Kluyveromyces* species and *Saccharomyces* species. Particularly preferred expression hosts may be selected from *Aspergillus niger, Aspergillus niger* var. *tubigenis, Aspergillus niger* var. *awamori, Asperillus aculeatis, Aspergillus nidulans, Aspergillus orveae, Trichoderma reesei, Bacillus subtilis, Bacillus licheniformis; Bacillus amyloliquefaciens, Kluyeromyces lactis* and *Saccharomyces cerevisiae.*

General teachings on the transformation of fungi and yeasts are presented in following sections.

Another host organism can be a plant A review of the general techniques used for transforming plants may be found in articles by Potrykus (*Annu Rev Plant Physiol Plant Mol Biol [1991]* 42:205-225) and Christou (Agro-Food-Industry Hi-Tech March/April 1994 17-27). Further teachings on plant transformation may be found in EP-A-0449375.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect the host organism can be of the genus *Aspergillus*, such as *Aspergillus niger*.

A transformed *Aspergillus* according to the present invention can also be prepared by following, for example, the teachings of Turner G. 1994 (Vectors for genetic manipulation In: Martinelli S. D., Kinghorn. J. R. (Editors) *Aspergillus*: 50 years on. Progress in industrial microbiology vol 29. Elsevier Amsterdam. 1994. pp. 641-666).

Gene expression in filamentous fungi has been reviewed in Punt et al. (2002) Trends Biotechnol 2002 May; 20(5):200, Archer & Peberdy Crit Rev Biotechnol (1997) 17(4):273-306.

Transformed Yeast

In another embodiment, the transformed organism can be a yeast

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1): 45-66), may be used as a vehicle for heterologous gene expression.

A review of the principles of heterologous gene expression in *Saccharomyces cerevisiae* and section of gene products is given by E Hinchcliffe E Kenny (1993, "Yeast as a vehicle for the expression of heterologous genes", Yeast, Vol. 5, Anthony H Rose and J Stuart Harrison, eds, 2nd edition, Academic Press Ltd.).

For the information of yeast, several transformation protocols have been developed. For example, a transformed *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers such as auxotrophic markers dominant antibiotic resistance markers.

Culturing and Production

Host cells transformed with the nucleotide sequence of the present invention may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme.

In yet further aspect, the present invention relates to a method of producing variants of the invention, which method comprises cultivating a host cell as described herein under conditions which are suitable for the production of the variant and recovering the variant from the cells and/or culture medium.

The protein produced by a recombinant cell may be displayed on the surface of the cell.

The enzyme may be secreted from the host cells and may conveniently be recovered from the culture medium using well-known procedures.

Secretion

Often, it is desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Isolation of Variants

The α-amylase family variants secreted from the host cells may be conveniently recovered from the culture medium by well-known procedures, including separating the cells from the medium by centrifugation or filtration and precipitating protein fraction by means of a salt such as ammonium sulfate, followed by the use of chromatographic procedures such as ion exchange chromatography, affinity chromatography or the like.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Testing for α-Amylase Family Variants

Variants produced by any of the methods described herein may be tested, either prior to or after purification for reduction in endo-amylase activity and increase in hydrolysis activity when compared to the reference and/or parent enzyme.

Accordingly, microorganisms capable of expressing the variant of interest is incubated in a suitable medium and under suitable conditions for selection of the variants.

Assays

The variants of the present invention were also tested for their hydrolysis activity which was determined by measuring the increase in reducing power according to (Penninga et al., (1995) *Biochemistry,* 34: 3368-3376).

Endo-activity was determined using a the PHADEBAS test (PHARMACIA), which is a cross-linked starch substrate that can only be cleaved by endo-activity. The substrate (1 tablet in 4 ml sodium citrate buffer, pH 6.0 and 10 mM calcium chloride) was incubated with 0.1-1 mg/ml enzyme and 10 microliter samples were taken at regular intervals and added to 0.9 ml 0.2 M sodium hydroxide to stop the reaction. After spinning down (5 min) the absorbance was measured at 620 nm. Endo-activity is expressed as the change in absorbance per min. The activity of wild-type CGTase is defined as 100%.

Fusion Proteins

The amino acid sequence for use according to the present invention may be produced as a fusion protein, for example to aid in extraction and purification. Preferably, the fusion protein will not hinder the activity of the protein sequence.

Isolated

In one aspect, preferably the enzyme or nucleotide sequence for same or a product obtained by use of either of same is in an isolated form. The term "isolated" means that the enzyme or nucleotide sequence for same or a product obtained by use of either of same is at least substantially free from at least one other component with which the enzyme or nucleotide sequence for same is naturally associated in nature and as found in nature. It will be understood that the protein may be mixed with carriers or diluents which will not interfere with the intended purpose of the protein and still be regarded as substantially isolated

Purified

In one aspect, preferably the enzyme or nucleotide sequence for same or a product obtained by use of either of same is in a purified form. The term "purified" means that the enzyme or nucleotide sequence for same or a product

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand though base pairing" as well as the process of amplification as carried out in polymerase chain reaction (PCR) technologies.

The hybridisation referred to herein indicates that the analogous DNA sequence hybridises to the nucleotide sequence corresponding to the protein encoding part of the nucleic acid sequences shown as SEQ ID 1, SEQ ID 2 or SEQ ID 3, under at least low stringency conditions as described herein.

Suitable experimental conditions for determining hybridisation at low stringency between a nucleotide probe and a homologous DNA or RNA sequence involves pre-soaking a filter containing the DNA fragments or RNA to hybridise in 5×SSC (sodium chloride/sodium citrate, Sambrook et al., (1989) Molecular cloning, a laboratory manual, Cold Spring Laboratory press, New York) for 10 minutes, and pre-hybridisation of the filter in a solution of 5×SSC, 5×Denhardt's solution, 0.5% SDS and 100 μg/ml of denatured sonicated salmon sperm DNA, followed by hybridisation of in the same solution containing a random, $^{32}$P-dCTP-labeled (specific activity >1×109 cmp/μg) probe for 12 hours at 45° C. The filter is then washed twice for 30 minutes in 2×SSC, 0.5% SDS in at least 55° C. (for low stringency), at least 60° C. (for medium stringency), more preferably at least 65° C. (medium/high stringency), more preferably at least 70° C. (for high stringency), and even more preferably at least 75° C. (for very high stringency).

Molecules which hybridise to the oligonucleotide probe under the above conditions may be detected for example by exposure to X-ray film.

Uses

The α-amylase family variants of the invention possess valuable properties which may be advantageously used in various industrial applications. In particular, the enzyme finds potential application for retarding or preventing retrogradation, and thus the staling, of starch based food common in the baking industry.

In a further aspect, the variant of the present invention is used for the preparation of bakery products or foodstuff. For certain aspects, preferably the foodstuff is a bakery product—such as bread, or other dough based products such as pastry prepared in accordance with conventional techniques known in the art.

The alpha-amylase variant may be used as the only enzyme or in combination with one or more additional enzymes, such as xylanase, lipase, glucose oxidase and other oxidoreductases, or an amylolytic enzyme.

Some variants are particularly useful in a process for the manufacture of linear oligosaccharides, or in the production of sweeteners and ethanol from starch, and/or for textile desizing. Conditions for conventional starch, conversion processes, including starch liquefaction and/or saccharification processes are known.

Therefore, in another aspect, the present invention provides CGTase variants for use in a process for the manufacture of linear oligosaccharides, in particular linear oligosaccharides of 2 to 12 glucose units, preferably linear oligosaccharides 2 to 9 glucose units.

Large Scale Application

In one preferred embodiment of the present invention, the amino acid sequence is used for large scale applications.

Preferably the amino acid sequence is produced in a quantity of from 1 g per liter to about 2 g per liter of the total cell culture volume after cultivation of the host organism.

Preferably the amino acid sequence is produced in a quantity of from 100 mg per liter to about 900 mg per liter of the total cell culture volume after cultivation of the host organism.

Preferably the amino acid sequence is produced in a quantity of from 250 mg per liter to about 500 mg per liter of the total cell culture volume after cultivation of the host organism.

Food

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

Food Ingredient

The composition of the present invention may be used as a food ingredient.

As used herein the term "food ingredient" includes a formulation, which is or can be added to functional foods or foodstuffs and includes formulations which can be used at low levels in a wide variety of products that require, for example, acidifying or emulsifying.

The food ingredient may be in the from of a solution or as a solid—depending on the use and/or the mode of application and/or the mode of administration.

Food Supplements

The composition of the present invention may be—or may be added to—food supplements.

Functional Foods

The composition of the present invention may be—or may be added to—functional foods.

As used herein, the term "functional food" means food which is capable of providing not only a nutritional effect and/or a taste satisfaction, but is also capable of delivering a further beneficial effect to consumer.

Although there is no legal definition of a functional food, most of the parties with an interest in this area agree that they are foods marketed as having specific health effects.

Food Products

The composition of the present invention can be used in the preparation of food products such as one or more of confectionery products, dairy products and/or bakery products.

For certain aspects, preferably the foodstuff is a bakery product—such as bread, pastry, biscuits or cookies.

The present invention also provides a method of preparing a food or a food ingredient, the method comprising admixing the enzyme or a product produced by said enzyme with another food ingredient. The method for preparing or a food ingredient is also another aspect of the present invention.

Recombinant DNA Techniques

Although in general any molecular techniques mentioned herein are well known in the art, reference may be made in particular to Sambrooks et al., Molecular Cloning, A Laboratory Manual (1989) and Ausubel et al., Short Protocols in Molecular Biology (1999) 4$^{th}$ Ed, John Wiley & Son, Inc.

EXAMPLES

The invention is further illustrated with reference to the following experimental procedures and examples which are not intended to be in any way limiting to the scope of the invention as claimed.

FIGURES AND TABLES

FIG. 1. Schematic overview of the interactions between a maltononaose substrate and the substrate binding cleft of *B. circulans* CGTase.

Figure 2:
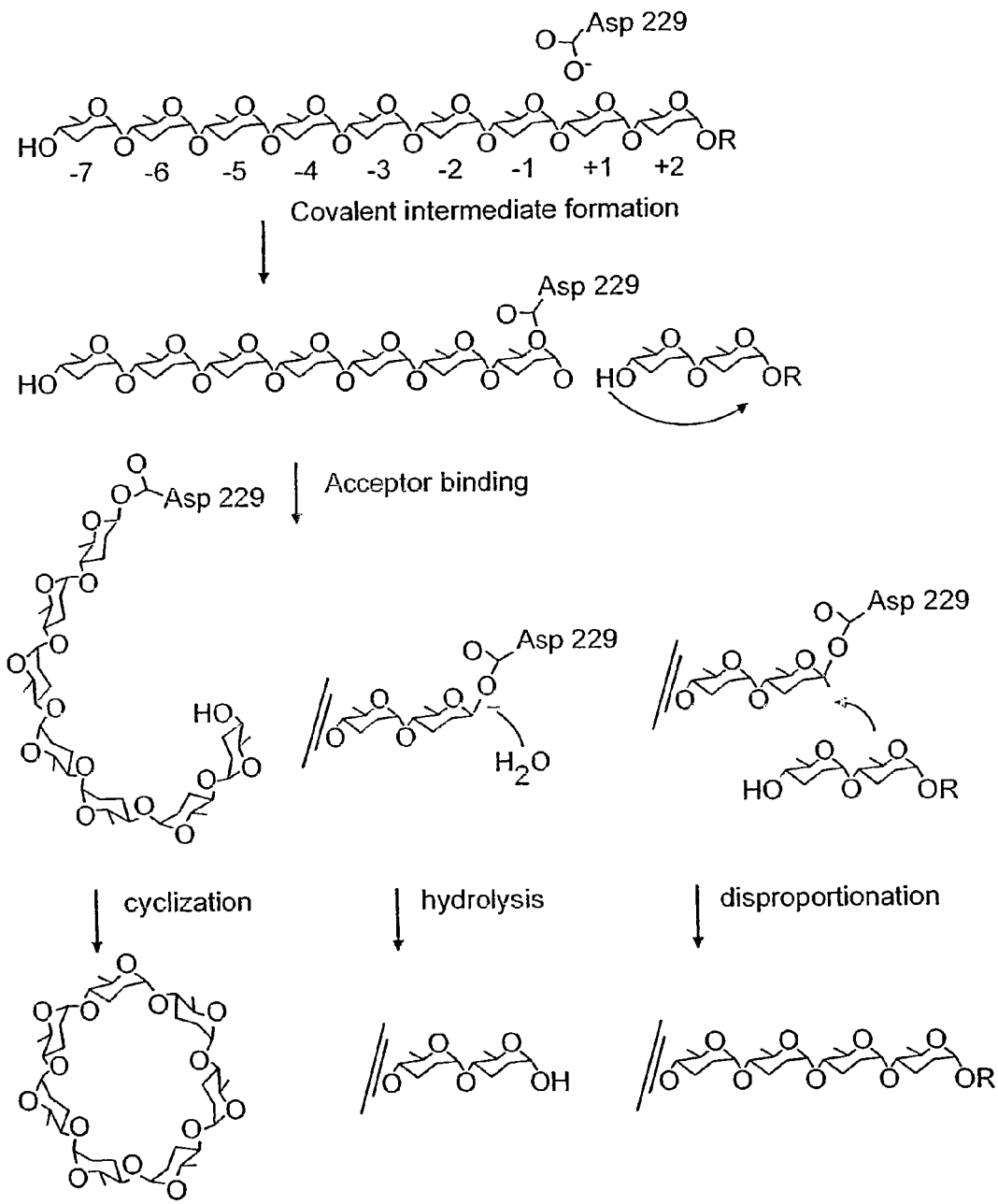

FIG. 2. Schematic representation of the reactions catalyzed by CGTase.

Figure 3:
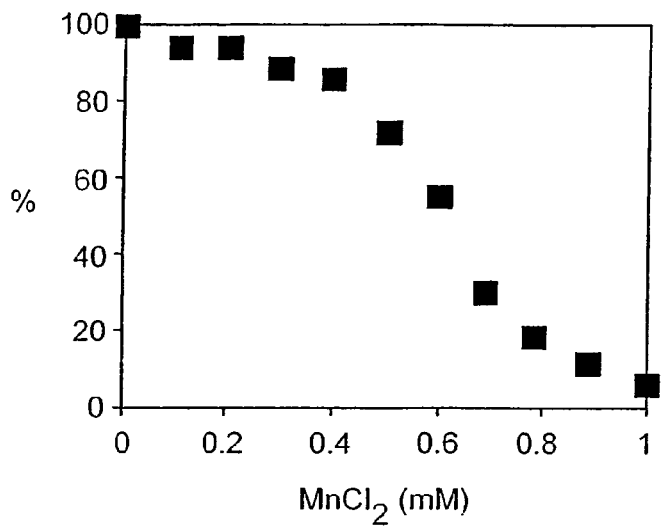

FIG. 3. Percentage of clones that expressed an active starch degrading CGTase.

FIG. 5. Sequence alignment.

Table I. Hydrolysis and endo-activities of BC251 and *Tabium* CGTase variants at 50° C.

DETAILED DESCRIPTION OF THE FIGURES

FIG. 1.

Schematic overview of the interactions between a maltononaose substrate and the substrate binding cleft of *B. circulans* CGTase. The arrow indicates the scissile bond between subsites −1 and +1; hydrogen bonds are shown as dashed lines. Arg47 and Asn94 do not interact with uncleaved substrate, but they do interact with the reaction intermediate and the product γ-cyclodextrin, respectively (16;41). Phe183 and Phe259 have hydrophobic stacking interaction with the sugar rings. For clarity not all interactions at the −2, −1 and +1 subsites are shown. The figure has been adapted from (5).

FIG. 2

Schematic representation of the reactions catalyzed by CGTase. After bond cleavage a covalently bound reaction enzyme-glucosyl intermediate is formed. In the second step of the reaction the reaction intermediate is transferred to an acceptor molecule. In the cyclization reaction the terminal OH-4 group of the covalently linked oligosaccharide is used as acceptor, whereas water or a second sugar are used as acceptors in the hydrolysis and disproportionation reactions, respectively. This figure has been adapted from reference (23).

FIG. 3.

Percentage of clones that expressed an active starch degrading CGTase (on LB starch plates) as a function of the MnCl$_2$ concentration used during PCR amplification of the BC251 cgt gene.

FIG. 4

Close-up view of the A230V mutant structure (black) superimposed on the structure of *B. circulans* D229N/E257Q. CGTase with bound maltononaose (grey)(5). For clarity only the substrate binding subsites −2 to +2 are shown. The valine side chain of mutant A230V would form a close contact (1.9 Å) with the O3 atom of the glucose in acceptor subsite +1 of the maltononaose structure (the alanine side chain is at 3.2 Å).

FIG. 5.

Figure 4:
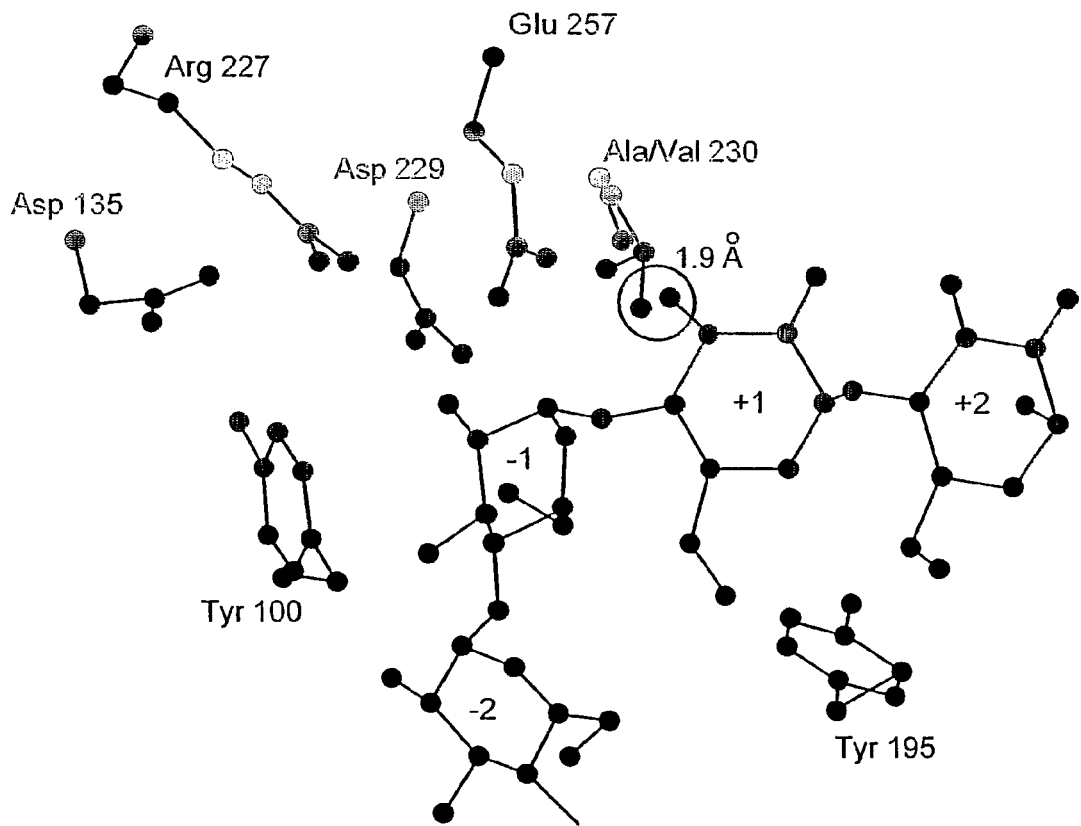

This shows the sequence alignment presented as FIG. 4 in U.S. Pat. No. 6,482,622.

FIG. 6.

This is a continuation of the sequence alignment depicted in FIG. 5.

EXPERIMENTAL PROCEDURES

Structural Determination

Crystals of BC251 CGTase mutant A230V were grown from 60% v/v 2-methyl-2,4-pentanediol, 100 mM HEPES buffer, pH 7.5, and 5% w/v maltose (17). Data were collected at 100 K on an in house MARCCD system (MarUSA Inc., Evanston, USA) with a diameter of 165 mm and using CuKa radiation from a BrukerNonius FR591 rotating-anode generator equipped with Osmic mirrors. Processing was done with DENZO and SCALEPACK (18). The structure of CGTase liganded with maltotetraose (PDB code 1CXF) with all waters and sugars removed was used as starting model. Refinement was done with CNS (19). Ligands were placed in sigmaA-weighted 2Fo-Fc and Fo-Fc electron density maps using the program O (20). The atomic co-ordinates and the structure factors of mutant A230V have been deposited with the Protein Data Bank (www.rcsb.org).

Bacterial Strains and Plasmids

*Escherichia coli* MC1061 (21) was used for DNA manipulations and *Bacillus subtilis* DB104A (22) was used for protein production. The plasmids pDP66k- (7) and pCScgt-tt (23), with the cgt genes of BC251 and *Thermoanaerobacterium thermosulfurigenes* strain EM1 (*Tabium*), respectively, were used for mutagenesis and protein production. Plasmid carrying strains were grown on LB medium (24) at 37° C. in the presence of kanamycin, 50 or 6 μg/ml for *E. coli* or *B. subtilis*, respectively. When appropriate, potato starch (1.5% w/v) was added to LB-agar plates to identify colonies expressing a starch degrading CGTase. Transformation of *B. subtilis* was done according to Bron (25).

Site-Directed Mutagenesis

Mutations and restriction sites were introduced into pDP66k- and pCScgt-tt as described (7;11) and verified by DNA sequencing. The XhoI and KpnI restriction sites introduced into pDP66k- resulted in V6S and A678G mutations (near the N- and C-termini, respectively), which had no measurable effect on the cyclization, disproportionation, and hydrolysis activities of BC251 CGTase (data not shown).

The primers used were as follows:

```
F1 (XhoI),
5'-GCGCCGGATACCTCGAGTTCCAACAAGCAAAATTTC-'3

R1 (KpnI),
5'-CCAATTCACGTTAATGGTACCGGTGCCGCTGGACGG-'3;

F21L,
5'-ATCTATCAAATTTTGACCGACAGGTTT-'3;

R47W,
5'-ACGAACCTCTGGCTGTATTGC-'3;

N94S,
5'-TCCGGCGTGAACAGCACGGCCTAT-'3;

A245T,
5'-TTTATGGCTACCGTCAACAAC-'3;

Q320L,
5'-GTGGATGACCTGGTGACGTTC-'3;

A357T,
5'-GGCGTCCCCACCATTTATTAC-'3;

V660A,
5'-GGATCCACCGCCACGTGGGAA-'3;

A231V,
5'-ATACGTCTAGATGTTGTAAAACATATG-'3.
```

Mutated nucleotides and restriction sites are underlined.

Saturation Mutagenesis

Ala230 of BC251 CGTase was replaced by all nineteen other amino acid residues. The mutations were introduced using the site-directed mutagenesis procedure, as described herein, using the primer

5'-ATCCGCATGGATNNSGTGAAGCATATG-3'
(A230X).

N is A+G+C+T,

S is G+C and

X is any amino acid residue.

Error-Prone PCR Mutagenesis

The BC251 cgt gene was amplified from pDP66k- with the primers F1 and R1. PCR mixtures (50 µl) contained: 1×Taq DNA polymerase buffer 1 mM MgSO$_4$, 0-1 mM MnCl$_2$, 0.6 mM of each dNTP, 0.07 µM of each primer, 20 ng template and 2.5 units Taq DNA polymerase (Roche). PCR reactions were performed for 25 cycles: 30 sec 94° C., 40 sec 54° C., and 2 min 72° C. The PCR products were restricted with XhoI and KpnI, and the resulting fragment (2016 bp) was extracted from agarose gel (QIAquick Gel Extraction Kit; Qiagen) and cloned in pDP66k-, replacing the wild-type cgt gene. The XhoI site is 12 nucleotides beyond the sequence coding for the export signal of CGTase (CGTase is an extracelluar enzyme) and the KpnI site is 30 nucleotides before the stop codon of the gene.

DNA Sequencing

Cycle sequencing (26) was performed on double-stranded-DNA using the Thermo sequence fluorescent primer cycle sequence kit (Amersham Phamacia Biotech AB) and the reactions were run on the Pharmacia ALF-Express sequencing machine at BMTC (Groningen, The Netherlands). Error-prone PCR mutants were double-stranded sequenced (six sequence reactions per mutant).

Selection of CGTase Variants with Increased Hydrolytic Activity

Ligation mixtures of the error-prone PCR products and the plasmid pDP66- were transformed to *E. coli* MC1061, plated on LB-agar plates and the resulting colonies were transferred to 200 µl LB medium in 96-well microtiter-plates, using the Q-pix (Genetix, New Milton Hamsphire, UK). After overnight incubation 750 rpm), 25 µl of each culture was transferred to a second microtiter-plate containing 25 µl bacterial protein extraction reagent (Pierce, Rockford, Ill.) per well to lyse the cells. Subsequently, 200 µl of 1% (w/v) soluble starch (Lamers and Pleuger, Wijnegen, Belgium) in 10 mM sodium citrate buffer (pH 6.0) was added and the microtiter-plates were incubated at 50° C. for 2 h in an oven. The amount of reducing sugars formed was measured using an adapted version of the Nelson-Somogyi assay (27;28). Forty µl of the reaction was added to 40 µl solution D in polypropylene microtiter-plates. After sealing the microtiter-plates with a polypropylene lid, they were incubated in an oven at 100° C. for 30 min. After cooling to room temp, 160 µl of solution E was added allowing color development within a few minutes. Microtiter-plates were either screened visually or the absorbance at 525 nm was measured. Solution D consisted of 25 ml solution A (25 g NaaCO$_3$, 25 g NaKtartrate and 200 g Na$_2$SO$_4$ in 1 L demi-water) and 1 ml solution B (30 g CuSO$_4$ 5H$_2$O and 0.2 ml sulfuric acid in 200 ml demi-water). Solution E consisted of 15.6 g (NH$_4$)$_6$Mo$_7$O$_{24}$ 4H$_2$O and 13.1 ml sulfuric acid in 950 ml demi-water plus 1.9 g Na$_2$HAsO$_4$ 7H$_2$O dissolved in 50 ml demi-water.

Enzyme Assays

CGTase proteins were produced and purified as described (29). All enzyme assays were done in 10 mM sodium citrate buffer (pH 6.0) at 50° or 60° C. for BC251 and *Tabium* CGTase, respectively. Cyclization activities were determined by incubating 0.1-0.5 µg enzyme/ml with 2.5% (w/v) partially hydrolyzed potato starch (Paselli SA2; Avebe, Foxhol, The Netherlands). The amount of β-cyclodextrin formed was measured with phenolphthalein (30). The disproportionation activity was determined as described (13;31), using 0.1 µg enzyme/ml, 1 mM 4-nitrophenyl-α-D-maltoheptaoside-4-6-O-ethylidene (EPS; Megazyme, County Wicklow, Ireland) and 10 mM maltose as donor and acceptor substrates, respectively. The hydrolysis activity was determined by measuring the increase in reducing power upon incubation of 0.5-5 µg enzyme/ml with 1% (w/v) soluble starch (Lamers & Pleuger, Wijnegen, Belgium) (29).

Structure Comparison

Three-dimensional structures were displayed and compared using the Swiss-PdbViewer version 3.7 (2) (32) and the program O (20). Figures were made using the Swiss-Pdb-Viewer and Pov-Ray for Windows version 3.1 g. The BC251 CGTase structures used were entries 1CDG (17) and 1CXK (5) from the ProteinData Bank (33).

Example 1

Error-Prone PCR Conditions

Optimal error-prone PCR mutagenesis conditions were determined by amplifying the BC251, cgt gene (SEQ ID 4) at ten different MnCl$_2$ concentrations. The PCR products were cloned in plasmid pDP66k-, transformed into *E. coli* and plated on LB plates complemented with starch. Only colonies expressing a star degrading CGTase form a halo around the colony. The percentage of halo forming colonies decreased with increasing MnCl$_2$ concentrations (FIG. 3), indicating that the number of inactivating mutations increased with higher MnCl$_2$ concentrations. A MnCl$_2$ concentration of 0.2-0.3 mM was chosen as optimal error-prone PCR condition, with about 90% of the (mutant) CGTase clones obtained at this MnCl$_2$ concentration retaining starch degrading activity (FIG. 3).

Example 2

Variants were Designed in Order to Obtain an Increase in Hydrolysis Activity

In order to select for CGTase variants with increased hydrolytic activity approximately 12,000 clones were assayed for hydrolytic activity in the first round of mutagenesis and selection. The MnCl$_2$ concentrations used in the PCRs were 0.2 mM (6,000 clones) and 0.3 mM (6,000 clones). Twenty-two clones had a significantly increased hydrolytic activity. Plasmid DNA was isolated from each positive clone and subsequently used to produce and purify the encoded mutant proteins. All 22 mutant CGTases had higher hydrolytic and lower cyclization activities than wild-type CGTase. Some mutants had even a higher hydrolytic than cyclization activity.

The hydrolytic activity of CGTase was further enhanced in a second and third round of mutagenesis, using 0.25 mM MnCl$_2$ during PCR amplification. Mutants 6 and 6-2 were used as PCR templates in the second and third round of mutagenesis, respectively; these variants had the highest hydrolytic activity after their rounds of mutagenesis. About 10,000 clones each were assayed for hydrolytic activity in the second and third rounds of mutagenesis resulting in four and eight clones with increased hydrolytic activity, respectively. Plasmid DNA of the positive clones was isolated and the encoded proteins were produced and purified. The mutant CGTases identified in the second round had much higher hydrolytic activities than the parent mutant 6. Surprisingly, the cyclization activities had also increased, although we selected for increased hydrolytic activity. The hydrolytic activity had further increased after the third round of mutagenesis, whereas the cyclization activity was unaffected or lowered compared to the parent mutant 6-2. Thus, a mutant CGTase with an almost 10-fold reduced cyclization activity and a 90-fold increased hydrolytic activity was obtained in only three rounds of mutagenesis and selection.

DNA Sequencing of the Variants which Exhibited Increase Hydrolase Activity

Of the 34 selected CGTase variants with enhanced hydrolytic activity, 22 were subjected to nucleotide sequencing (2016 bp). This revealed 41 nucleotide substitutions and 31 amino acid mutations, of which 15 amino acid mutations were different. Additional stop-codons were not found, which was in agreement with the wild-type size of all selected mutant proteins on SDS-PAGE (data not shown). The mutants had one to three nucleotide mutations (1.9 on average) per round of mutagenesis, which resulted in one or two amino acid mutations (1.4 on average). The variations in mutation frequency were small (<10% at the DNA and the amino acid level) for the individual rounds of mutagenesis and the different MnCl$_2$ concentrations used (0.2, 0.25 and 0.3 mM). The substitutions A for G, T for C, C for T and G for A were observed most frequently, whereas A for C, T for A or G, C for G and G for T mutations were not found. The frequent observation of T for C and C for T mutations is due to the selection applied, as these changes were required to obtain the amino acid mutations causing the increased hydrolytic activity.

Example 3

Mutations Enhancing Hydrolytic Activity

The twelve mutants displaying the highest hydrolytic activity after the first round of mutagenesis had either a F259S (4 times) or an A230V (SEQ ID 1) (8 times) mutation, with or without a second mutation. The second round of mutagenesis yielded a F21L mutation (3 times) and once the combination A245T/T357F, in addition to the A230V/V660A mutations. After the third round of mutagenesis the mutations N8S, R47W, N94S and Q320L were identified, although N8S was identified in combination with N94S only. Of the mutations with clearly enhanced hydrolytic activity, three mutations were in residues located in the substrate binding cleft at subsite −3 (Arg47), subsite +1 (Ala230), and subsite +2 (Phe259) (FIG. 1), and one mutation occurred in residue that has no direct interactions with substrates (Phe21).

Surprisingly, the variants with increased hydrolysis rate were found to have a strong reduced of hydrolysis of hydrolysis to endo-amylase activity demonstrating that the exo-specificity of these variants was strongly improved (Table I).

Site-Directed Mutants

Of the 15 different amino acid mutations identified, seven mutations (N8S, I215V, N299D, T514A, K655E, V660A and A672G) were only found in combination with a second mutation (A230V, F259S or N94S). Comparison of the single A230V, F259S and N94S mutants with the double mutants showed that these seven mutations made no additional contribution to hydrolysis activities. For mutant V660A this was confirmed; it has similar activities as wild-type CGTase.

To analyze the individual effects of the other eight mutations F21L, R47W, A230V, A245T, F295S, Q320L and A357T, they were introduced as single mutation in wild-type CGTase. It appeared that N94S, A245T, Q320L and A357T hardly altered the hydrolytic activity, whereas F21L, R47W, A230V and F259S clearly caused an increased hydrolytic activity compared with wild-type CGTase. In addition, these eight mutations lowered the cyclization and disproportionation activities, except mutant R47W, which had a higher disproportionation activity. In particular, mutant A230V drastically lowered the cyclization and disproportionation activity. Thus, several residues (Phe21, Arg47, Ala230 and Phe259) important for the low hydrolytic activity of CGTase were identified.

Saturation Mutagenesis

Since error-prone PCR mutagenesis cannot introduce all possible mutations at, a single position (34), the position of Ala230 was also investigated with saturation mutagenesis. Five hundred clones were assayed for hydrolytic and cyclization activity. Most clones (70%) had at most 5% of wild-type cyclization activity, whereas none of them had an increased cyclization activity, showing the importance of this residue for the cyclization reaction. Forty clones (8%) had a strongly increased hydrolytic activity. Eight of them were randomly selected for sequencing; all of them contained the A230V mutation (SEQ ID 1). Thus, the mere change of an alanine to a valine side chain at position 230 is sufficient to strongly increase the hydrolytic activity and decrease the cyclization activity of CGTase.

Example 4

*Tabium* CGTase

SEQ ID 5

Mutation A230V was also introduced into *Tabium* CGTase (A231V, *Tabium*, *Bacillus circulans* CGTase numbering, SEQ ID 2), as this CGTase has a relatively high hydrolytic activity compared to most other CGTases (35). Similar to the effects in BC251 CGTase, the A231V mutation strongly reduced the cyclization and increased the hydrolytic activity of *Tabium* CGTase. In an attempt to further enhance the hydrolytic activity of this CGTase, the double mutant A231V/F260E was constructed, since until now *Tabium* mutant F260E had the highest hydrolytic activity ever described for a CGTase (11). However, the double mutant had an even lower hydrolytic activity than wild-type *Tabium* CGTase, indicating that the two single mutations are mutually exclusive and not additive.

Example 5

Mutation A230V has been found to substantially change the product and substrate specificity of cyclodextrin glycosyltransferases. (CGTase); i.e. CGTase is converted from a transferase into a hydrolase and the exo-specificity is increased >14 fold in one CGTase (TABIUM) and >100 fold in another (BC 251) (see Table 1).

Since Novamyl is structurally very closely related to CGTases and contains the corresponding residue A229 in the same position and confirmation the equivalent mutation A229V will most likely increase the exo-specificity of Novamyl significantly, and thereby improve its antistaling functionality considerably (see U.S. Pat. No. 6,482,622 showing sequence alignment of Novamyl® with CGTAse from *Thermoanaerobacterium thermosulfurigenes*, *Bacillus circulans* and *Thermoanaerobacter* (see FIG. 5).

Novamyl has both endo and exo-amylase activity which results in starch being processed by random cleaving of the polysaccharide molecule which weakens its structure and therefore its water absorbing property.

Thus, the present invention provides for the possibility of developing Novamyl® variants (or alternative like SAS) with increased exo-amylase activity and optionally reduced endo-amylase activity which would find great commercial application as this would provide a variant enzyme which is capable of processing starch from the end and thus not weaken its structure and therefore its water absorbing capacity.

Example 6

Malogenic α-Amylase Novamyl®

SEQ ID 6

Mutation A230V was also introduced into maltogenic α-amylase Novamyl®(A229V, Novamyl®, SEQ ID 3). This enzyme is taught in EP 120 693 (available from Novo Nordisk A/S, Denmark).

The A229V mutation was found to lead to a strong increase in the ration of hydrolysis to endo-activity and thus a significant improvement in exo-specificity.

Furthermore, similar effects were seen from changing A229 to all other residues than G or A by saturation mutagenesis.

Combinations of A299V and Y258X mutations (with X being non-aromatic residues) were found to be even more effective in increasing the exo-specificity of the variants.

All publications mentioned herein are hereby incorporated by reference. Various modifications and variations of the described methods and system of the present invention may be apparent to those skilled in the art without departing from the scope and spirit of the present invention. Although the present invention has been described in connection with specific preferred embodiments, it should be understood that the invention as claimed should not be unduly limited to, such specific embodiments. Indeed, various modifications of the described modes for carrying out the invention which are obvious to those skilled in biochemistry and biotechnology or related fields are intended to be within the scope of the following claims.

TABLE 1

Hydrolysis and endo-activities of BC251 and Tabium CGTase variants at 50° C.

| | Mg/ml protein | Endo-activity | Hydrolysis activity | Hydrolysis/Endo-activity |
|---|---|---|---|---|
| BC251 CGTase | | | | |
| Wild-type | 1.33 | 100 | 4 | 0.04 |
| Error-prone mutants | | | | |
| A230V (15) | 0.20 | 18 | 77 | 4.3 |
| A230V/F21L (25) | 0.30 | 31 | 182 | 5.9 |
| A230V/A245T/A357T (26) | 0.39 | 32 | 163 | 5.1 |
| A230V/F21L/N94S (31) | 0.50 | 47 | 260 | 5.5 |
| A230V/F21L/R47W | 0.22 | 49 | 250 | 5.1 |
| Other mutants | | | | |
| R47L | 0.32 | 86 | 7 | 0.08 |
| R47Q | 0.19 | 108 | 1 | 0.01 |
| K232L | 1.10 | 54 | | |
| E264A | 2.60 | 82 | | |
| Y663A (MBS2) | 0.18 | 86 | | |
| Y633A/R47L | 0.25 | 55 | | |
| Y633A/R47Q | 0.51 | 74 | | |
| W616A/W662A (MBS1) | 0.42 | 96 | | |
| L600A (MBS2) | 0.79 | 130 | | |
| TABIUM CGTase | | | | |
| Wild-type | 0.40 | 100 | 54 | 0.54 |
| A231V | 0.06 | 19 | 138 | 7.3 |
| A231V/F260E | | | 21 | |
| A231V/F260I | | 7.5 | 135 | 18 |
| F260I | | 52 | 174 | 3.3 |

REFERENCES

1. Henrissat, B. and Davies, G. (1997) *Curr. Opin. Struct. Biol.* 7, 637-644.
2. Takata. H., Kuriki, T., Okada, S., Takesada, Y., Iizuka, M., Minamiura, N., and Imanaka, T. (1992) *J. Biol. Chem.* 267, 18447-18452.
3. Svensson, B. (1994) *Plant Mol. Biol.* 25, 141-157.
4. McCarter, J. D. and Withers, S. G. (1994) *Curr. Opin. Struct. Biol.* 4, 885-892.

5. Uitdehaag, 3. C. M., Mosi, R., Kalk, K. H., van der Veen, B. A, Dijkhuizen, L., Withers, S. G., and Dijkstra, B. W. (1999) *Nature Struct. Biol.* 6, 432-436.
6. Kuriki, T. and Imanaka, T. (1999) *J. Biosci. Bioeng.* 87, 557-565.
7. Penninga, D., van derVeen, B. A, Knegtel, R. M., van Hijum, S. A. F. T., Rozeboom, H. J., Kalk, K. H., Dijkstra, B. W., and Dijkhuizen, L. (1996) *J. Biol. Chem.* 271, 32777-32784.
8. Ohdan, K., Kuriki, T., Takata, H., Kaneko, H., and Okada, S. (2000) *Appl. Environ. Microbiol.* 66, 3058-3064.
9. van der Veen, B. A., Van Alebeek, G. J., Uitdehaag, J. C. M., Dijkstra, B. W., and Dijkuizen, L. (2000) *Eur. J. Biochem.* 267, 658-665.
10. van der Veen, B. A., Leemhuis, H., Kralj, S., Uitdchaag, J. C. M., Dijkstra, B. W., and Dijkuizen, L. (2001) *J. Biol. Chem.* 276, 44557-44562.
11. Leemhuis, H., Dijkstra, B. W., and Dijkhuizen, L. (2002) *FEBS Lett.* 514, 189-192.
12. Fujiwara, S., Kakihara, H, Sakaguchi, K, and Imanaka, T. (1992) *J. Bacteriol.* 174, 7478-7481.
13. van derVeen, B. A., Uitdehaag, J. C. M., Penninga, D., Van Alebeek, G. J., Smith, L. M., Dijkstra, B. W., and Dijkhuizen, L. (2000) *J. Mol. Biol.* 296, 1027-1038.
14. van der Veen, B. A., Uitdehaag, J. C. M., Dijkstra, B. W., and Dijkhuizen, L. (2000) *Eur. J. Biochem.* 267, 3432-3441.
15. Leemhuis, H., Uitdehaag, J. C. M., Rozeboom, H. J., Dijkstra, B. W., and Dijkhuizen, L. (2002) *J. Biol. Chem.* 277, 1113-1119.
16. Uitdehaag, J. C. M., Van Alebeek, G. J., van der Veen, B. A., Dijkhuizen, L., and Dijkstra, B. W. (2000) *Biochemistry* 39, 7772-7780.
17. Lawson, C. L., van Montfort, R., Strokopytov, B., Rozeboom, H. J., Kalk, K. H., de Vries, G. E., Penninga, D, Dijkhuizen, L., and Dijkstra, B. W. (1994) *J. Mol. Biol.* 236, 590-600.
18. Otwinowski, Z. (1993) in *Data collection and Processing* (Sawyer, L., Isaacs, N., and Bailey, S., Eds.) pp 56-62, SERC Laboratory, Daresbury, UK.
19. Brünger, A. T., Adams, P. D., Clore, G. M., DeLano, W. L., Gros, P., Grosse-Kunstleve, R. W., Jiamg, J.-S., Kuszewski, J., Nilges, M., Pannu, N. S., Read, R. J., Rice, L. M., Simonson, T., and Warren, G. L. (1998) *Acta Cryst.* D54, 905-921.
20. Jones, T. A, Zou, J. Y., Cowan, S. W., and Kjeldgaard, M. (1991) *Acta Crysallogr.* A47, 110-119.
21. Meissner, P. S., Sisk, W. P., and Berman, M. L. (1987) *Pros Natl. Acad Sci. U.S.A.* 84, 4171-4175.
22. Smith, H., de Jong, A., Bron, S., and Venema, G. (1988) *Gene* 70, 351-361.
23. Leemhuis, H., Dijkstra, B. W., and Dijkhuizen, L. (2003) *Eur. J. Biochem.* 270, 155-162.
24. Sambrook, J., Frisch, E. J., and Maniatis, T. (1989) *Molecular cloning: a labatory manual* Cold Spring Harbor Laboratory Press, New York.
25. Bron, S. (1990) in *Modern mirobiological methods for Bacillus* (Harwood C. R. and Cutting, S. M., Eds.) pp 146-147, John Wiley & Sons, New York/Chichester.
26. Murray, V. (1989) *Nucleic Acid Res.* 17, 8889.
27. Somogyi, M. (1952) *J. Biol. Chem.* 195, 19-23.
28. Nelson, N. (2002) *J. Biol. Chem.* 153, 375-380.
29. Penninga, Strokopytov, B., Rozeboom, H. J., Lawson, C. L., Dijkstra, B. W., Bergman, J., and Dijkhuzin, L. (1995) *Biochemistry* 34, 3368-3376.
30. Vikmon, M. Rapid and simple spectrophotometric method for determination of microamounts of cyclodextrins, in *Proceedings of the first international symposium on cyclodextrins* (Szejlti, J. Ed.), pp 64-74, Reidel Publishing Co, Dordrecht, The Netherlands.
31. Nakamura, A., Haga, K., and Yamane, K. (1994) *FEBS Lett.* 337, 66-70.
32. Guex, N. and Peitsch, M. C. (1997) *Electrophoresis* 18, 2714-2723.
33. Berman, H. M., Westbrok, J., Feng, Z., Gilliland, G., Bhat, T. N., Weissig, H., Shindyalov, I. N., and Bourne, P. E. (2000) *Nucleic Acids Res.* 28, 235-242.
34. Leung, D. W., Chen, E., and Goeddel, D. V. (1989) *Technique* 1, 11-15.
35. Wind, R. D., Liebl, W., Buitelaar, R. M., Penninga, D., Spreinat, A., Dijkhuizen, L., and Bahl, H. (1995) *Appl. Environ. Microbiol.* 61, 1257-1265.
36. Nakamura, A., Haga, K, and Yamane, K. (1994) *Biochemistry* 33, 9929-9936.
37. Nakamura, A., Haga, K., and Yamane, K. (1993) *Biochemistry* 32, 6624-6631.
38. Kim, Y. H., Bae, K. H., Kim, T. J., Park, K. H., Lee, H. S., and Byun, S. M. (1997) *Biochem Mol. Biol. Int.* 41, 227-234.
39. Mattsson, P., Battchikova, N, Sippola, K, and Korpela, T. (1995) *Biochim. Biophys. Acta* 1247, 97-103.
40. Strokopytov, B., Knegtel, R. M., Penninga, D., Rozeboom, H. J., Kalk, K. H., Dijkhuizen, L., and Dijkstra, B. W. (1996) *Biochemistry* 35, 4241-4249.
41. Uitdehaag, J. C. M., Kalk, K. H., van der Veen, B. A., Dijkhuizen, L., and Dijkstra, B. W. (1999) *J. Biol. Chem.* 274, 34868-34876.
42. Wind, R. D., Uitdehaag, J. C. M., Buitelaar, R. M., Dijkstra, B. W., and Dijkhuizen, L. (1998) *J. Biol. Chem.* 273, 5771-5779.
43. Nakajima, R., Imanaka, T., and Aiba, S. (1986) *Appl. Microbiol. Biotechnol.* 23, 355-360.
44. Nielsen, J. E., Beier, L., Otzen, D., Bochert, T. V., Frantzen, H. B., Andersen, K. V., and Svendsen, A. (1999) *Eur. J. Biochem.* 264, 816-824.
45. Uitdehaag, J. C. M., van der Veen. B. A., Dijkuizen, L., and Dijkstra, B. W. (2002) *Enzyme Microb. Technol.* 30, 295-304.

The invention claimed is:

1. An isolated and/or purified cyclodextrin glycosyltransferase (CGTase) polypeptide with increased hydrolase activity, comprising the amino acid sequence as set forth in SEQ ID NO: 1 or 3, wherein
 (a) said CGTase polypeptide has a variation at position 230, A230V, and
 (b) said CGTase polypeptide optionally has amino acid substitutions selected from the group consisting of F21L, A245T, A357T, N94S, R47W, R47L, R47Q, K232L, E264A, Y633A, W616A, W662A, L600A, A231V, F260E, and F260I.

2. The CGTase polypeptide according to claim 1 wherein said CGTase polypeptide on incubation with starch has a lower endo-amylase activity than the reference enzyme under the same conditions.

3. The CGTase polypeptide according to claim 1 or 2, wherein said CGTase polypeptide is prepared from DNA that has been mutated such that the resultant transcription product is or comprises said CGTase polypeptide.

4. A method of using an enzyme variant according to claim 1 in preparing a food product, wherein the food product is optionally a bakery product, and wherein the method optionally comprises one or more of the following steps:
 (i) admixing the enzyme variant with at least one additional food ingredient or foodstuff ingredient,
 (ii) packaging said food product,
 (iii) labeling said packaged food product as a food product.

5. A process of treating starch comprising contacting the starch with a variant enzyme and allowing the enzyme to generate from the starch one or more linear products, and wherein the enzyme variant is an enzyme variant according to claim 1.

* * * * *